(12) United States Patent
Kobayashi et al.

(10) Patent No.: US 12,241,095 B2
(45) Date of Patent: Mar. 4, 2025

(54) MODIFIED HEAT-RESISTANT DNA POLYMERASE

(71) Applicant: TOYOBO CO., LTD., Osaka (JP)

(72) Inventors: Tetsuhiro Kobayashi, Tsuruga (JP); Yasuhiro Arai, Tsuruga (JP)

(73) Assignee: TOYOBO CO., LTD., Osaka (JP)

( * ) Notice: Subject to any disclaimer, the term of this patent is extended or adjusted under 35 U.S.C. 154(b) by 43 days.

(21) Appl. No.: 17/839,101

(22) Filed: Jun. 13, 2022

(65) Prior Publication Data

US 2022/0348892 A1    Nov. 3, 2022

Related U.S. Application Data

(62) Division of application No. 16/461,268, filed as application No. PCT/JP2017/040694 on Nov. 13, 2017, now abandoned.

(30) Foreign Application Priority Data

Nov. 22, 2016    (JP) .................. 2016-226546
Sep. 5, 2017    (JP) .................. 2017-170159
Oct. 31, 2017    (JP) .................. 2017-210452

(51) Int. Cl.
*C12N 9/12*    (2006.01)
*C12P 19/34*    (2006.01)
*C12Q 1/686*    (2018.01)

(52) U.S. Cl.
CPC .......... *C12N 9/1276* (2013.01); *C12Q 1/686* (2013.01); *C12Y 207/07049* (2013.01)

(58) Field of Classification Search
None
See application file for complete search history.

(56) References Cited

U.S. PATENT DOCUMENTS

| | | | |
|---|---|---|---|
| 5,455,170 A | 10/1995 | Abramson et al. | |
| 9,315,787 B2 | 4/2016 | Schafer et al. | |
| 2003/0096987 A1 | 5/2003 | Uematsu et al. | |
| 2003/0104378 A1 | 6/2003 | Allawi et al. | |
| 2011/0104682 A1 | 5/2011 | Allawi et al. | |
| 2011/0281305 A1 | 11/2011 | Bourn et al. | |
| 2014/0030765 A1 | 1/2014 | Schafer et al. | |
| 2014/0170730 A1 | 6/2014 | Suko | |
| 2014/0322793 A1 | 10/2014 | Ishino et al. | |
| 2021/0254035 A1 | 8/2021 | Kobayashi et al. | |

FOREIGN PATENT DOCUMENTS

| | | | |
|---|---|---|---|
| CN | 103966182 A | 8/2014 | |
| JP | H05-317058 A | 12/1993 | |
| JP | H09-019292 A | 1/1997 | |
| JP | 2004-521606 A | 7/2004 | |
| JP | 2012-507987 A | 4/2012 | |
| JP | 5189101 B2 | 4/2013 | |
| JP | 5809059 B2 | 11/2015 | |
| JP | 2015-536684 A | 12/2015 | |
| JP | 5852650 B2 | 2/2016 | |
| JP | 2017-108735 A | 6/2017 | |
| JP | 2017-108736 A | 6/2017 | |
| WO | WO2003004632 | * 1/2003 | |
| WO | WO 2008/046612 A1 | 4/2008 | |
| WO | WO 2011/014885 A1 | 2/2011 | |
| WO | WO 2012/097318 A2 | 7/2012 | |

OTHER PUBLICATIONS

U.S. Appl. No. 16/461,268, filed May 15, 2019.
Airaksinen et al., "Modified base compositions at degenerate positions of a mutagenic oligonucleotide enhance randomness in site-saturation mutagenesis," *Nucleic Acids Research*, 26(2): 576-581 (1998).
Arezi et al., "Compartmentalized self-replication under fast PCR cycling conditions yields Taq DNA polymerase mutants with increased DNA-binding affinity and blood resistance," *Front. Microbiol.*, 5: 408 (2014).
Folz et al., "Substrate Specificity of Eukaryotic Signal Peptidase," *J. Biol. Chem.*, 263(4): 2070-2078 (1988).
Kermekchiev et al., "Mutants of Taq DNA polymerase resistant to PCR inhibitors allow DNA amplification from whole blood and crude soil samples," *Nucleic Acids Res.*, 37(5): e40 (2009).
Yamagami et al., "Mutant Taq DNA polymerases with improved elongation ability as a useful reagent for genetic engineering," *Front. Microbiol.*, 5: 461 (2014).
European Patent Office, Extended European Search Report in European Patent Application No. 17874693.9 (May 19, 2020).
Japanese Patent Office, International Search Report in International Patent Application No. PCT/JP2017/040694 (Jan. 30, 2018).
Japanese Patent Office, Notice of Reasons for Refusal in Japanese Patent Application No. 2018-552507 (Jul. 27, 2021).
China National Intellectual Property Administration, Office Action in Chinese Patent Application No. 201780071770.7 (Aug. 17, 2022).
Imanaka, "Thermostabilization and Functional Conversion of Enzymes by Protein Engineering," 39(7): 504-507 (1990).

(Continued)

*Primary Examiner* — Manjunath N Rao
*Assistant Examiner* — Jae W Lee
(74) *Attorney, Agent, or Firm* — Leydig, Voit & Mayer, Ltd.

(57) ABSTRACT

The present invention provides DNA polymerases that are highly resistant to inhibitors, and that can shorten the entire nucleic acid amplification reaction time by shortening the reverse transcription reaction time in a nucleic acid amplification method, in particular, in PCR or RT-PCR. The DNA polymerase is characterized by having reverse transcription activity, and comprising at least one amino acid modification at position 509 or 744 in SEQ ID NO: 1 or 2. In particular, the amino acid modification at position 509 or 744 in SEQ ID NO: 1 or 2 is substitution with histidine, lysine, or arginine.

7 Claims, 11 Drawing Sheets

Specification includes a Sequence Listing.

(56) References Cited

OTHER PUBLICATIONS

Japan Patent Office, Office Action in Japanese Patent Application No. 2022-032680 (Apr. 18, 2023).

* cited by examiner

1 E9K
2 P6P/E9K
3 P6S
4 K53N/K56Q/E57D
5 S30N/K53N/K56Q/E57D
6 S30N
7 D238N
8 Q509R
9 Q509K
10 E744K
11 E799G
12 E799G/E800A
13 wt

1 E9K
2 P6P/E9K
3 P6S
4 K53N/K56Q/E57D
5 S30N/ K53N/K56Q/E57D
6 S30N
7 D238N
8 Q509R
9 Q509K
10 E744K
11 E799G
12 E799G/E800A
13 wt

| RT 1min | w.t. | Q509R | E744K |
|---|---|---|---|
| 10ng | 23.90 | 14.08 | 14.29 |
| 1ng | 24.74 | 17.86 | 17.92 |
| 0.1ng | 25.60 | 21.43 | 21.37 |
| 0.01ng | 27.60 | 24.60 | 24.62 |
| Slope | -1.20 | -3.51 | -3.44 |
| r² | 0.947 | 0.998 | 0.999 |
| PCR efficiency | 586% | 93% | 95% |

Amplification curve　　　　Melting curve w.t.　　　　w.t.

Q509R　　　　Q509R

E744K　　　　E744K

Amplification curve w.t.

Q509R

E744K

Melting curve w.t.

Q509R

E744K

Amplification curve  Melting curve w.t.  w.t.

Q509R  Q509R

E744K  E744K

1 Tth DNA Polymerase
2 Tth Q509K
3 Tth Q509R
4 Taq DNA Polymerase
5 Taq E507K
6 Taq E507R

|  | Wt | Q509R |
|---|---|---|
| E. Coli genome  5ng | 28.62 | 17.98 |
| 0.5ng | 37.33 | 21.70 |
| 0.05ng | Undetermined | 25.42 |
| 0.005ng | 37.43 | 28.52 |
| Slope | -2.52 | -3.54 |
| $r^2$ | 0.5808 | 0.998 |
| PCR efficiency | 149% | 92% | w.t.

Q509R

| Copy number | Q509R | Wt |
|---|---|---|
| 2500 | 32.27 | 34.87 |
| 625 | 34.38 | 37.74 |
| 156 | 36.41 | - |
| 40 | 39.10 | - |
| 40 | 39.31 | - |
| 24.4 | 40.72 | - |
| 24.4 | 40.60 | 40.31 |
| NTC | - | - |

Q509R wt

SEQUENCE LISTING

```
<160> NUMBER OF SEQ ID NOS: 82

<210> SEQ ID NO 1
<211> LENGTH: 834
<212> TYPE: PRT
<213> ORGANISM: Thermus thermophilus HB8

<400> SEQUENCE: 1

Met Glu Ala Met Leu Pro Leu Phe Glu Pro Lys Gly Arg Val Leu Leu
1               5                   10                  15

Val Asp Gly His His Leu Ala Tyr Arg Thr Phe Phe Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Tyr Lys Ala Val Phe
    50                  55                  60
```

-continued

```
Val Val Phe Asp Ala Lys Ala Pro Ser Phe Arg His Glu Ala Tyr Glu
 65                  70                  75                  80

Ala Tyr Lys Ala Gly Arg Ala Pro Thr Pro Glu Asp Phe Pro Arg Gln
                 85                  90                  95

Leu Ala Leu Ile Lys Glu Leu Val Asp Leu Leu Gly Phe Thr Arg Leu
            100                 105                 110

Glu Val Pro Gly Tyr Glu Ala Asp Asp Val Leu Ala Thr Leu Ala Lys
            115                 120                 125

Lys Ala Glu Lys Glu Gly Tyr Glu Val Arg Ile Leu Thr Ala Asp Arg
            130                 135                 140

Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Arg
                165                 170                 175

Pro Glu Gln Trp Val Asp Phe Arg Ala Leu Val Gly Asp Pro Ser Asp
            180                 185                 190

Asn Leu Pro Gly Val Lys Gly Ile Gly Glu Lys Thr Ala Leu Lys Leu
            195                 200                 205

Leu Lys Glu Trp Gly Ser Leu Glu Asn Leu Leu Lys Asn Leu Asp Arg
210                 215                 220

Val Lys Pro Glu Asn Val Arg Glu Lys Ile Lys Ala His Leu Glu Asp
225                 230                 235                 240

Leu Arg Leu Ser Leu Glu Leu Ser Arg Val Arg Thr Asp Leu Pro Leu
                245                 250                 255

Glu Val Asp Leu Ala Gln Gly Arg Glu Pro Asp Arg Glu Gly Leu Arg
            260                 265                 270

Ala Phe Leu Glu Arg Leu Glu Phe Gly Ser Leu Leu His Glu Phe Gly
            275                 280                 285

Leu Leu Glu Ala Pro Ala Pro Leu Glu Glu Ala Pro Trp Pro Pro Pro
            290                 295                 300

Glu Gly Ala Phe Val Gly Phe Val Leu Ser Arg Pro Glu Pro Met Trp
305                 310                 315                 320

Ala Glu Leu Lys Ala Leu Ala Ala Cys Arg Asp Gly Arg Val His Arg
                325                 330                 335

Ala Ala Asp Pro Leu Ala Gly Leu Lys Asp Leu Lys Glu Val Arg Gly
            340                 345                 350

Leu Leu Ala Lys Asp Leu Ala Val Leu Ala Ser Arg Glu Gly Leu Asp
            355                 360                 365

Leu Val Pro Gly Asp Asp Pro Met Leu Leu Ala Tyr Leu Leu Asp Pro
            370                 375                 380

Ser Asn Thr Thr Pro Glu Gly Val Ala Arg Arg Tyr Gly Gly Glu Trp
385                 390                 395                 400

Thr Glu Asp Ala Ala His Arg Ala Leu Leu Ser Glu Arg Leu His Arg
                405                 410                 415

Asn Leu Leu Lys Arg Leu Glu Gly Glu Glu Lys Leu Leu Trp Leu Tyr
            420                 425                 430

His Glu Val Glu Lys Pro Leu Ser Arg Val Leu Ala His Met Glu Ala
            435                 440                 445

Thr Gly Val Arg Leu Asp Val Ala Tyr Leu Gln Ala Leu Ser Leu Glu
            450                 455                 460

Leu Ala Glu Glu Ile Arg Arg Leu Glu Glu Glu Val Phe Arg Leu Ala
465                 470                 475                 480
```

```
Gly His Pro Phe Asn Leu Asn Ser Arg Asp Gln Leu Glu Arg Val Leu
            485                 490                 495

Phe Asp Glu Leu Arg Leu Pro Ala Leu Gly Lys Thr Gln Lys Thr Gly
            500                 505                 510

Lys Arg Ser Thr Ser Ala Ala Val Leu Glu Ala Leu Arg Glu Ala His
            515                 520                 525

Pro Ile Val Glu Lys Ile Leu Gln His Arg Glu Leu Thr Lys Leu Lys
            530                 535                 540

Asn Thr Tyr Val Asp Pro Leu Pro Ser Leu Val His Pro Arg Thr Gly
545                 550                 555                 560

Arg Leu His Thr Arg Phe Asn Gln Thr Ala Thr Ala Thr Gly Arg Leu
                565                 570                 575

Ser Ser Ser Asp Pro Asn Leu Gln Asn Ile Pro Val Arg Thr Pro Leu
            580                 585                 590

Gly Gln Arg Ile Arg Arg Ala Phe Val Ala Glu Ala Gly Trp Ala Leu
            595                 600                 605

Val Ala Leu Asp Tyr Ser Gln Ile Glu Leu Arg Val Leu Ala His Leu
            610                 615                 620

Ser Gly Asp Glu Asn Leu Ile Arg Val Phe Gln Glu Gly Lys Asp Ile
625                 630                 635                 640

His Thr Gln Thr Ala Ser Trp Met Phe Gly Val Pro Pro Glu Ala Val
                645                 650                 655

Asp Pro Leu Met Arg Arg Ala Ala Lys Thr Val Asn Phe Gly Val Leu
            660                 665                 670

Tyr Gly Met Ser Ala His Arg Leu Ser Gln Glu Leu Ala Ile Pro Tyr
            675                 680                 685

Glu Glu Ala Val Ala Phe Ile Glu Arg Tyr Phe Gln Ser Phe Pro Lys
            690                 695                 700

Val Arg Ala Trp Ile Glu Lys Thr Leu Glu Glu Gly Arg Lys Arg Gly
705                 710                 715                 720

Tyr Val Glu Thr Leu Phe Gly Arg Arg Tyr Val Pro Asp Leu Asn
            725                 730                 735

Ala Arg Val Lys Ser Val Arg Glu Ala Ala Glu Arg Met Ala Phe Asn
            740                 745                 750

Met Pro Val Gln Gly Thr Ala Ala Asp Leu Met Lys Leu Ala Met Val
            755                 760                 765

Lys Leu Phe Pro Arg Leu Arg Glu Met Gly Ala Arg Met Leu Leu Gln
            770                 775                 780

Val His Asp Glu Leu Leu Leu Glu Ala Pro Gln Ala Arg Ala Glu Glu
785                 790                 795                 800

Val Ala Ala Leu Ala Lys Glu Ala Met Glu Lys Ala Tyr Pro Leu Ala
                805                 810                 815

Val Pro Leu Glu Val Glu Val Gly Met Gly Glu Asp Trp Leu Ser Ala
            820                 825                 830

Lys Gly

<210> SEQ ID NO 2
<211> LENGTH: 834
<212> TYPE: PRT
<213> ORGANISM: Thermus sp Z05

<400> SEQUENCE: 2

Met Lys Ala Met Leu Pro Leu Phe Glu Pro Lys Gly Arg Val Leu Leu
1               5                   10                  15
```

Val Asp Gly His His Leu Ala Tyr Arg Thr Phe Phe Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Tyr Lys Ala Val Phe
    50                  55                  60

Val Val Phe Asp Ala Lys Ala Pro Ser Phe Arg His Glu Ala Tyr Glu
65                  70                  75                  80

Ala Tyr Lys Ala Gly Arg Ala Pro Thr Pro Glu Asp Phe Pro Arg Gln
                85                  90                  95

Leu Ala Leu Ile Lys Glu Leu Val Asp Leu Leu Gly Phe Thr Arg Leu
            100                 105                 110

Glu Val Pro Gly Phe Glu Ala Asp Asp Val Leu Ala Thr Leu Ala Lys
        115                 120                 125

Lys Ala Glu Arg Glu Gly Tyr Glu Val Arg Ile Leu Thr Ala Asp Arg
    130                 135                 140

Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Lys
                165                 170                 175

Pro Glu Gln Trp Val Asp Phe Arg Ala Leu Val Gly Asp Pro Ser Asp
            180                 185                 190

Asn Leu Pro Gly Val Lys Gly Ile Gly Glu Lys Thr Ala Leu Lys Leu
        195                 200                 205

Leu Lys Glu Trp Gly Ser Leu Glu Asn Ile Leu Lys Asn Leu Asp Arg
    210                 215                 220

Val Lys Pro Glu Ser Val Arg Glu Arg Ile Lys Ala His Leu Glu Asp
225                 230                 235                 240

Leu Lys Leu Ser Leu Glu Leu Ser Arg Val Arg Ser Asp Leu Pro Leu
                245                 250                 255

Glu Val Asp Phe Ala Arg Arg Arg Glu Pro Asp Arg Glu Gly Leu Arg
            260                 265                 270

Ala Phe Leu Glu Arg Leu Glu Phe Gly Ser Leu Leu His Glu Phe Gly
        275                 280                 285

Leu Leu Glu Ala Pro Ala Pro Leu Glu Glu Ala Pro Trp Pro Pro Pro
    290                 295                 300

Glu Gly Ala Phe Val Gly Phe Val Leu Ser Arg Pro Glu Pro Met Trp
305                 310                 315                 320

Ala Glu Leu Lys Ala Leu Ala Ala Cys Lys Glu Gly Arg Val His Arg
                325                 330                 335

Ala Lys Asp Pro Leu Ala Gly Leu Lys Asp Leu Lys Glu Val Arg Gly
            340                 345                 350

Leu Leu Ala Lys Asp Leu Ala Val Leu Ala Leu Arg Glu Gly Leu Asp
        355                 360                 365

Leu Ala Pro Ser Asp Asp Pro Met Leu Leu Ala Tyr Leu Leu Asp Pro
    370                 375                 380

Ser Asn Thr Thr Pro Glu Gly Val Ala Arg Arg Tyr Gly Gly Glu Trp
385                 390                 395                 400

Thr Glu Asp Ala Ala His Arg Ala Leu Leu Ala Glu Arg Leu Gln Gln
                405                 410                 415

Asn Leu Leu Glu Arg Leu Lys Gly Glu Glu Lys Leu Leu Trp Leu Tyr
            420                 425                 430

Gln Glu Val Glu Lys Pro Leu Ser Arg Val Leu Ala His Met Glu Ala

```
                    435                 440                 445
Thr Gly Val Arg Leu Asp Val Ala Tyr Leu Lys Ala Leu Ser Leu Glu
450                 455                 460

Leu Ala Glu Glu Ile Arg Arg Leu Glu Glu Val Phe Arg Leu Ala
465                 470                 475                 480

Gly His Pro Phe Asn Leu Asn Ser Arg Asp Gln Leu Glu Arg Val Leu
                    485                 490                 495

Phe Asp Glu Leu Arg Leu Pro Ala Leu Gly Lys Thr Gln Lys Thr Gly
                500                 505                 510

Lys Arg Ser Thr Ser Ala Ala Val Leu Glu Ala Leu Arg Glu Ala His
                515                 520                 525

Pro Ile Val Glu Lys Ile Leu Gln His Arg Glu Leu Thr Lys Leu Lys
530                 535                 540

Asn Thr Tyr Val Asp Pro Leu Pro Gly Leu Val His Pro Arg Thr Gly
545                 550                 555                 560

Arg Leu His Thr Arg Phe Asn Gln Thr Ala Thr Ala Thr Gly Arg Leu
                    565                 570                 575

Ser Ser Ser Asp Pro Asn Leu Gln Asn Ile Pro Ile Arg Thr Pro Leu
                580                 585                 590

Gly Gln Arg Ile Arg Arg Ala Phe Val Ala Glu Ala Gly Trp Ala Leu
                595                 600                 605

Val Ala Leu Asp Tyr Ser Gln Ile Glu Leu Arg Val Leu Ala His Leu
610                 615                 620

Ser Gly Asp Glu Asn Leu Ile Arg Val Phe Gln Glu Gly Lys Asp Ile
625                 630                 635                 640

His Thr Gln Thr Ala Ser Trp Met Phe Gly Val Ser Pro Glu Ala Val
                    645                 650                 655

Asp Pro Leu Met Arg Arg Ala Ala Lys Thr Val Asn Phe Gly Val Leu
                660                 665                 670

Tyr Gly Met Ser Ala His Arg Leu Ser Gln Glu Leu Ala Ile Pro Tyr
                675                 680                 685

Glu Glu Ala Val Ala Phe Ile Glu Arg Tyr Phe Gln Ser Phe Pro Lys
690                 695                 700

Val Arg Ala Trp Ile Glu Lys Thr Leu Glu Glu Gly Arg Lys Arg Gly
705                 710                 715                 720

Tyr Val Glu Thr Leu Phe Gly Arg Arg Arg Tyr Val Pro Asp Leu Asn
                    725                 730                 735

Ala Arg Val Lys Ser Val Arg Glu Ala Ala Glu Arg Met Ala Phe Asn
                740                 745                 750

Met Pro Val Gln Gly Thr Ala Ala Asp Leu Met Lys Leu Ala Met Val
                755                 760                 765

Lys Leu Phe Pro His Leu Arg Glu Met Gly Ala Arg Met Leu Leu Gln
770                 775                 780

Val His Asp Glu Leu Leu Leu Glu Ala Pro Gln Ala Arg Ala Glu Glu
785                 790                 795                 800

Val Ala Ala Leu Ala Lys Glu Ala Met Glu Lys Ala Tyr Pro Leu Ala
                    805                 810                 815

Val Pro Leu Glu Val Glu Val Gly Ile Gly Glu Asp Trp Leu Ser Ala
                820                 825                 830

Lys Gly

<210> SEQ ID NO 3
<211> LENGTH: 2505
```

<212> TYPE: DNA
<213> ORGANISM: Thermus thermophilus HB8

<400> SEQUENCE: 3

| | | | | | |
|---|---|---|---|---|---|
| atggaggcga | tgcttccgct | ctttgaaccc | aaaggccggg | tcctcctggt | ggacggccac | 60 |
| cacctggcct | accgcacctt | cttcgccctg | aagggcctca | ccacgagccg | gggcgaaccg | 120 |
| gtgcaggcgg | tctacggctt | cgccaagagc | ctcctcaagg | ccctgaagga | ggacgggtac | 180 |
| aaggccgtct | tcgtggtctt | tgacgccaag | gcccctcct | tccgccacga | ggcctacgag | 240 |
| gcctacaagg | cggggagggc | ccgaccccc | gaggacttcc | cccggcagct | cgccctcatc | 300 |
| aaggagctgg | tggacctcct | ggggtttacc | cgcctcgagg | tccccggcta | cgaggcggac | 360 |
| gacgttctcg | ccaccctggc | caagaaggcg | aaaaggagg | ggtacgaggt | gcgcatcctc | 420 |
| accgccgacc | gcgacctcta | ccaactcgtc | tccgaccgcg | tcgccgtcct | ccaccccgag | 480 |
| ggccacctca | tcaccccgga | gtggcttttgg | gagaagtacg | gcctcaggcc | ggagcagtgg | 540 |
| gtggacttcc | gcgccctcgt | ggggacccc | tccgacaacc | tccccggggt | caagggcatc | 600 |
| ggggagaaga | ccgccctcaa | gctcctcaag | gagtggggaa | gcctggaaaa | cctcctcaag | 660 |
| aacctggacc | gggtaaagcc | agaaaacgtc | cgggagaaga | tcaaggccca | cctggaagac | 720 |
| ctcaggctct | ccttggagct | ctcccgggtg | cgcaccgacc | tcccctgga | ggtggacctc | 780 |
| gcccaggggc | gggagcccga | ccgggagggg | cttaggggcct | tcctggagag | gctggagttc | 840 |
| ggcagcctcc | tccacgagtt | cggcctcctg | gaggccccg | ccccctgga | ggaggccccc | 900 |
| tggccccgc | cggaagggc | cttcgtgggc | ttcgtcctct | cccgcccga | gcccatgtgg | 960 |
| gcggagctta | agccctggc | cgcctgcagg | gacggccggg | tgcaccgggc | agcagacccc | 1020 |
| ttggcggggc | taaaggacct | caaggaggtc | cggggcctcc | tcgccaagga | cctcgccgtc | 1080 |
| ttggcctcga | ggaggggct | agacctcgtg | cccggggacg | accccatgct | cctcgcctac | 1140 |
| ctcctggacc | cctccaacac | cacccccgag | gggtggcgc | ggcgctacgg | gggggagtgg | 1200 |
| acggaggacg | ccgccaccg | ggccctcctc | tcggagaggc | tccatcggaa | cctccttaag | 1260 |
| cgcctcgagg | gggaggagaa | gctcctttgg | ctctaccacg | aggtggaaaa | gccctctcc | 1320 |
| cgggtcctgg | cccacatgga | ggccaccggg | gtacggctgg | acgtggccta | ccttcaggcc | 1380 |
| cttttccctgg | agcttgcgga | ggagatccgc | cgcctcgagg | aggaggtctt | ccgcttggcg | 1440 |
| ggccacccct | tcaacctcaa | ctcccgggac | cagctgaaa | gggtgctctt | tgacgagctt | 1500 |
| aggcttcccg | ccttggggaa | gacgcaaaag | acaggcaagc | gctccaccag | cgccgcggtg | 1560 |
| ctggaggccc | tacgggaggc | ccaccccatc | gtggagaaga | tcctccagca | ccgggagctc | 1620 |
| accaagctca | agaacaccta | cgtggacccc | ctcccaagcc | tcgtccaccc | gaggacgggc | 1680 |
| cgcctccaca | cccgcttcaa | ccagacggcc | acggccacgg | ggaggcttag | tagctccgac | 1740 |
| cccaacctgc | agaacatccc | cgtccgcacc | cccttgggcc | agaggatccg | ccgggccttc | 1800 |
| gtggccgagg | cggttgggc | gttggtgcc | ctggactata | gccagataga | gctccgcgtc | 1860 |
| ctcgcccacc | tctccgggga | cgaaaacctg | atcagggtct | tccaggaggg | gaaggacatc | 1920 |
| cacacccaga | ccgcaagctg | gatgttcggc | gtccccccgg | aggccgtgga | cccctgatg | 1980 |
| cgccgggcgg | ccaagacggt | gaacttcggc | gtcctctacg | gcatgtccgc | ccataggctc | 2040 |
| tcccaggagc | ttgccatccc | ctacgaggag | gcggtggcct | ttatagagcg | ctacttccaa | 2100 |
| agcttccccca | aggtgcgggc | ctggatagaa | aagaccctgg | aggaggggag | gaagcggggc | 2160 |
| tacgtggaaa | ccctcttcgg | aagaaggcgc | tacgtgcccg | acctcaacgc | ccgggtgaag | 2220 |

| | |
|---|---:|
| agcgtcaggg aggccgcgga gcgcatggcc ttcaacatgc ccgtccaggg caccgccgcc | 2280 |
| gacctcatga agctcgccat ggtgaagctc ttcccccgcc tccgggagat gggggcccgc | 2340 |
| atgctcctcc aggtccacga cgagctcctc ctggaggccc cccaagcgcg ggccgaggag | 2400 |
| gtggcggctt tggccaagga ggccatggag aaggcctatc ccctcgccgt gcccctggag | 2460 |
| gtggaggtgg ggatggggga ggactggctt tccgccaagg gttag | 2505 |

<210> SEQ ID NO 4
<211> LENGTH: 2505
<212> TYPE: DNA
<213> ORGANISM: Artificial Sequence
<220> FEATURE:
<223> OTHER INFORMATION: Synthetic Sequence

<400> SEQUENCE: 4

| | |
|---|---:|
| atgaaagcaa tgctgccgct gtttgaaccg aaaggtcgtg ttctgctggt tgatggtcat | 60 |
| catctggcat atcgtacctt ttttgcactg aaaggtctga ccaccagtcg tggtgaaccg | 120 |
| gtgcaggcag tttatggttt tgccaaaagc ctgctgaaag ccctgaaaga gatggttat | 180 |
| aaagccgtgt ttgttgtgtt tgatgcaaaa gcaccgagct ttcgtcatga agcatatgaa | 240 |
| gcctataaag caggtcgtgc accgacaccg gaagattttc gcgtcagct ggcactgatt | 300 |
| aaagaactgg ttgatctgct ggttttacc cgtctggaag ttccgggttt tgaagcagat | 360 |
| gatgttctgg caaccctggc aaaaaaagca gaacgtgaag gttatgaagt tcgtattctg | 420 |
| accgcagatc gtgatctgta tcagctggtt agcgatcgtg ttgcagttct gcatccggaa | 480 |
| ggtcatctga ttacaccgga atggctgtgg gaaaaatatg gtctgaaacc ggaacagtgg | 540 |
| gttgattttc gtgcactggt tggtgatccg agcgataatc tgcctggtgt taaaggtatt | 600 |
| ggtgaaaaaa ccgcactgaa gctgttaaaa gaatggggta gcctggaaaa cattctgaaa | 660 |
| aatctggatc gtgttaaacc ggaaagcgtt cgtgaacgta ttaaagcaca tctggaagat | 720 |
| ctgaaactga gcctggaact gagccgtgtt cgtagcgatc tgccgctgga agttgatttt | 780 |
| gcacgtcgtc gcgaaccgga tcgtgaaggt ctgcgtgcat ttctggaacg tctggaattt | 840 |
| ggtagcctgc tgcatgaatt tggtctgctg aagcaccgg caccactgga agagccccct | 900 |
| tggcctccgc ctgaaggtgc atttgttggt tttgttctga gccgtccgga accgatgtgg | 960 |
| gcagaactga aagcactggc agcatgtaaa gaaggtcgcg ttcatcgggc aaaagatccg | 1020 |
| ctggcaggcc tgaaagattt aaaagaagtt cgcggactgc tggccaaaga tctggcagtt | 1080 |
| ctggcactgc gcgaaggtct ggatctggca ccgagtgatg atccgatgct gctggcctat | 1140 |
| ctgctggatc cgagcaatac cactccggaa ggcgttgccc gtcgttatgg tggtgaatgg | 1200 |
| accgaagatg cagcacatcg tgccctgctg cagaacgcc tgcagcagaa cctgctggaa | 1260 |
| cgcctgaaag gtgaagaaaa actgctgtgg ctgtatcaag aagttgaaaa accgctgtca | 1320 |
| cgtgttctgg cccatatgga agcaaccggt gttcgtctgg atgttgcata tctgaaagcg | 1380 |
| ctgtcactgg aactggcaga gaaattcgt cgcctggaag aggaagtttt tcgtctggca | 1440 |
| ggtcatccgt ttaatctgaa tagccgtgat cagctggaac gtgtgctgtt tgatgaactg | 1500 |
| cgtctgcctg cgctgggcaa aacccagaaa accggtaaac gtagcaccag cgcagccgtt | 1560 |
| ctggaagccc tgcgtgaagc catccgatt gttgaaaaaa tcctgcagca tcgtgaactg | 1620 |
| accaaactga aaaataccta tgtggatccg ctgcctggtc tggttcatcc gcgtaccggt | 1680 |
| cgtctgcata cccgttttaa tcagaccgca accgccaccg tcgcctgag cagcagcgat | 1740 |
| ccgaatctgc agaatattcc gattcgtaca ccgctgggtc agcgtattcg tcgtgccttt | 1800 |

| gttgcagaag caggttgggc attagttgca ctggattata gccagattga actgcgcgtt | 1860 |
| ctggcgcatc tgagcggtga tgaaaatctg attcgtgtgt ttcaagaggg caaagatatt | 1920 |
| catacccaga ccgccagctg gatgtttggt gttagtccgg aagcagttga tccgctgatg | 1980 |
| cgtcgtgcag caaaaaccgt taattttggt gttctgtatg gtatgagcgc acatcgtctg | 2040 |
| agccaagaac tggcaattcc gtatgaagaa gccgttgcat ttatcgaacg ttattttcag | 2100 |
| agctttccga agttcgtgc gtggattgaa aagaccttag aagaaggccg taaacgcggt | 2160 |
| tatgttgaaa ccctgtttgg tcgtcgtcgc tatgttccgg atctgaatgc acgtgttaaa | 2220 |
| tcagttcgtg aagcagccga acgtatggcc tttaatatgc cggttcaggg caccgcagca | 2280 |
| gatctgatga aactggccat ggttaaactg tttccgcatc tgcgtgaaat gggtgcacgt | 2340 |
| atgctgctgc aagttcatga tgagctgctg ttagaagcac cgcaggcacg tgcagaagaa | 2400 |
| gttgcagcac tggcgaaaga agcaatggaa aaagcatatc ctctggccgt tcctctggaa | 2460 |
| gtagaagttg gtattggcga agattggctg agcgcaaaag gttaa | 2505 |

<210> SEQ ID NO 5
<211> LENGTH: 2499
<212> TYPE: DNA
<213> ORGANISM: Thermus aquaticus

<400> SEQUENCE: 5

| atgcgcggca tgctgccgct gtttgagccc aagggccggg tcctcctggt ggacggccac | 60 |
| cacctggcct accgcacctt ccacgccctg aagggcctca ccaccagccg ggggagccg | 120 |
| gtgcaggcgg tctacggctt cgccaagagc ctcctcaagg ccctcaagga ggacggggac | 180 |
| gcggtgatcg tggtctttga cgccaaggcc ccctccttcc gccacgaggc ctacggggg | 240 |
| tacaaggcgg ccgggcccc cacgccggag gactttcccc ggcaactcgc cctcatcaag | 300 |
| gagctggtgg acctcctggg gctggcgcgc ctcgaggtcc cgggctacga ggcggacgac | 360 |
| gtcctggcca gcctggccaa gaaggcggaa aaggagggct acgaggtccg catcctcacc | 420 |
| gccgacaaag acctttacca gctcctttcc gaccgcatcc acgtcctcca ccccgagggg | 480 |
| tacctcatca ccccggcctg gctttgggaa aagtacggcc tgaggcccga ccagtgggcc | 540 |
| gactaccggg ccctgaccgg ggacgagtcc gacaaccttc cggggtcaa ggcatcggg | 600 |
| gagaagacgg cgaggaagct tctggaggag tgggggagcc tggaagccct cctcaagaac | 660 |
| ctggaccggc tgaagcccgc catccgggag aagatcctgg cccacatgga cgatctgaag | 720 |
| ctctcctggg acctggccaa ggtgcgcacc gacctgcccc tggaggtgga cttcgccaaa | 780 |
| aggcgggagc ccgaccggga gaggcttagg gcctttctgg agaggcttga gtttggcagc | 840 |
| ctcctccacg agttcggcct tctggaaagc cccaaggccc tggaggaggc ccctggccc | 900 |
| ccgccggaag ggcccttcgt gggctttgtg ctttcccgca aggagcccat gtgggccgat | 960 |
| cttctgccc tggccgccgc caggggggc gggtccacc gggcccccga gccttataaa | 1020 |
| gccctcaggg acctgaagga ggcgcggggg cttctcgcca aagacctgag cgttctggcc | 1080 |
| ctgagggaag gccttggcct cccgcccggc gacgaccca tgctcctcgc ctacctcctg | 1140 |
| gacccttcca acaccacccc cgaggggtg gccggcgct acgggggga gtggacggag | 1200 |
| gaggcggggg agcgggccgc cctttccgag aggctcttcg ccaacctgtg ggggaggctt | 1260 |
| gaggggggag agaggctcct ttggcttta cgggaggtgg agaggcccct ttccgctgtc | 1320 |
| ctggcccaca tggaggccac gggggtgcgc ctggacgtgg cctatctcag ggccttgtcc | 1380 |

```
ctggaggtgg ccgaggagat cgcccgcctc gaggccgagg tcttccgcct ggccggccac    1440
cccttcaacc tcaactcccg ggaccagctg gaaagggtcc tctttgacga gctagggctt    1500
cccgccatcg gcaagacgga gaagaccggc aagcgctcca ccagcgccgc cgtcctggag    1560
gccctccgcg aggcccaccc catcgtggag aagatcctgc agtaccggga gctcaccaag    1620
ctgaagagca cctacattga ccccttgccg gacctcatcc accccaggac gggccgcctc    1680
cacacccgct tcaaccagac ggccacggcc acgggcaggc taagtagctc cgatcccaac    1740
ctccagaaca tccccgtccg cacccegctt gggcagagga tccgccgggc cttcatcgcc    1800
gaggaggggt ggctattggt ggccctggac tatagccaga tagagctcag ggtgctggcc    1860
cacctctccg gcgacgagaa cctgatccgg gtcttccagg aggggcggga catccacacg    1920
gagaccgcca gctggatgtt cggcgtcccc cgggaggccg tggacccccct gatgcgccgg    1980 gcggccaaga ccatcaactt cggggtcctc tacggcatgt cggcccaccg cctctcccag    2040
gagctagcca tcccttacga ggaggccaag gccttcattg agcgctactt tcagagcttc    2100
cccaaggtgc gggcctggat tgagaagacc ctggaggagg caggaggcg ggggtacgtg    2160 gagaccctct tcggccgccg ccgctacgtg ccagacctag aggcccgggt gaagagcgtg    2220
cgggaggcgg ccgagcgcat ggccttcaac atgcccgtcc agggcaccgc cgccgacctc    2280
atgaagctgg ctatggtgaa gctcttcccc aggctggagg aaatgggggc caggatgctc    2340
cttcaggtcc acgacgagct ggtcctcgag gccccaaaag agagggcgga ggccgtggcc    2400
cggctggcca aggaggtcat ggaggggtg tatcccctgg ccgtgcccct ggaggtggag    2460
gtggggatag ggaggactg gctctccgcc aaggagtga                            2499

<210> SEQ ID NO 6
<211> LENGTH: 22
<212> TYPE: DNA
<213> ORGANISM: Artificial Sequence
<220> FEATURE:
<223> OTHER INFORMATION: Synthetic Sequence - The sequence of designed
      polynucleotide described in Example 3, 4 and 5

<400> SEQUENCE: 6
ggtgttccct tgatgtagca ca                                              22

<210> SEQ ID NO 7
<211> LENGTH: 26
<212> TYPE: DNA
<213> ORGANISM: Artificial Sequence
<220> FEATURE:
<223> OTHER INFORMATION: Synthetic Sequence - The sequence of designed
      polynucleotide described in Example 3, 4 and 5

<400> SEQUENCE: 7
acatgtattt gcatggaaaa caactc                                          26

<210> SEQ ID NO 8
<211> LENGTH: 35
<212> TYPE: DNA
<213> ORGANISM: Artificial Sequence
<220> FEATURE:
<223> OTHER INFORMATION: Synthetic Sequence - The sequence of designed
      polynucleotide described in Example 3

<400> SEQUENCE: 8
tgataggcac tgactctctg tcccttgggc tgttt                                35

<210> SEQ ID NO 9
```

```
<211> LENGTH: 35
<212> TYPE: DNA
<213> ORGANISM: Artificial Sequence
<220> FEATURE:
<223> OTHER INFORMATION: Synthetic Sequence - The sequence of designed
      polynucleotide described in Example 3

<400> SEQUENCE: 9
acatgattag caaaagggcc tagcttggac tcaga                                35

<210> SEQ ID NO 10
<211> LENGTH: 20
<212> TYPE: DNA
<213> ORGANISM: Artificial Sequence
<220> FEATURE:
<223> OTHER INFORMATION: Synthetic Sequence - The sequence of designed
      polynucleotide described in Example 6 and 7

<400> SEQUENCE: 10
agaaaatctg gcaccacacc                                                 20

<210> SEQ ID NO 11
<211> LENGTH: 20
<212> TYPE: DNA
<213> ORGANISM: Artificial Sequence
<220> FEATURE:
<223> OTHER INFORMATION: Synthetic Sequence - The sequence of designed
      polynucleotide described in Example 6 and 7

<400> SEQUENCE: 11
agaggcgtac agggatagca                                                 20

<210> SEQ ID NO 12
<211> LENGTH: 17
<212> TYPE: DNA
<213> ORGANISM: Artificial Sequence
<220> FEATURE:
<223> OTHER INFORMATION: Synthetic Sequence - The sequence of designed
      polynucleotide described in Example 8 and 11

<400> SEQUENCE: 12
cctccggccc ctgaatg                                                    17

<210> SEQ ID NO 13
<211> LENGTH: 18
<212> TYPE: DNA
<213> ORGANISM: Artificial Sequence
<220> FEATURE:
<223> OTHER INFORMATION: Synthetic Sequence - The sequence of designed
      polynucleotide described in Example 8 and 11

<400> SEQUENCE: 13
accggatggc caatccaa                                                   18

<210> SEQ ID NO 14
<211> LENGTH: 26
<212> TYPE: DNA
<213> ORGANISM: Artificial Sequence
<220> FEATURE:
<223> OTHER INFORMATION: Synthetic Sequence - The sequence of designed
      polynucleotide described in Example 8 and 11

<400> SEQUENCE: 14
ccgactactt tgggtgtccg tgtttc                                          26

<210> SEQ ID NO 15
<211> LENGTH: 22
```

```
<212> TYPE: DNA
<213> ORGANISM: Artificial Sequence
<220> FEATURE:
<223> OTHER INFORMATION: Synthetic Sequence - The sequence of designed
      polynucleotide described in Example 9

<400> SEQUENCE: 15
ttaggcctta gcgggcttag ac                                              22

<210> SEQ ID NO 16
<211> LENGTH: 22
<212> TYPE: DNA
<213> ORGANISM: Artificial Sequence
<220> FEATURE:
<223> OTHER INFORMATION: Synthetic Sequence - The sequence of designed
      polynucleotide described in Example 9

<400> SEQUENCE: 16
ccaggatttt tgatgggaca cg                                              22

<210> SEQ ID NO 17
<211> LENGTH: 21
<212> TYPE: DNA
<213> ORGANISM: Artificial Sequence
<220> FEATURE:
<223> OTHER INFORMATION: Synthetic Sequence - The sequence of designed
      polynucleotide described in Example 9

<400> SEQUENCE: 17
ccatgaagtc ggaatcgcta g                                               21

<210> SEQ ID NO 18
<211> LENGTH: 18
<212> TYPE: DNA
<213> ORGANISM: Artificial Sequence
<220> FEATURE:
<223> OTHER INFORMATION: Synthetic Sequence - The sequence of designed
      polynucleotide described in Example 10

<400> SEQUENCE: 18
actcccatgg tgtgacgg                                                   18

<210> SEQ ID NO 19
<211> LENGTH: 27
<212> TYPE: DNA
<213> ORGANISM: Artificial Sequence
<220> FEATURE:
<223> OTHER INFORMATION: Synthetic Sequence - The sequence of designed
      polynucleotide described in Example 10

<400> SEQUENCE: 19
cggtgaatac gttcccgggc cttgtac                                         27

<210> SEQ ID NO 20
<211> LENGTH: 20
<212> TYPE: DNA
<213> ORGANISM: Artificial Sequence
<220> FEATURE:
<223> OTHER INFORMATION: Synthetic Sequence - The sequence of designed
      polynucleotide described in Example 12

<400> SEQUENCE: 20
gagtgaaacc ttgcctcacg                                                 20

<210> SEQ ID NO 21
<211> LENGTH: 21
<212> TYPE: DNA
```

<210> SEQ ID NO 21
<211> LENGTH: 21
<212> TYPE: DNA
<213> ORGANISM: Artificial Sequence
<220> FEATURE:
<223> OTHER INFORMATION: Synthetic Sequence - The sequence of designed polynucleotide described in Example 12

<400> SEQUENCE: 21
catcttgagg cctcagcttt c    21

<210> SEQ ID NO 22
<211> LENGTH: 30
<212> TYPE: DNA
<213> ORGANISM: Artificial Sequence
<220> FEATURE:
<223> OTHER INFORMATION: Synthetic Sequence - The sequence of designed polynucleotide described in Example 12

<400> SEQUENCE: 22
cttgatgctc taccacatag gtctgggtac    30

<210> SEQ ID NO 23
<211> LENGTH: 23
<212> TYPE: DNA
<213> ORGANISM: Artificial Sequence
<220> FEATURE:
<223> OTHER INFORMATION: Synthetic Sequence - Primer

<400> SEQUENCE: 23
aagaagaccg gcaagcgctc cac    23

<210> SEQ ID NO 24
<211> LENGTH: 21
<212> TYPE: DNA
<213> ORGANISM: Artificial Sequence
<220> FEATURE:
<223> OTHER INFORMATION: Synthetic Sequence - Primer

<400> SEQUENCE: 24
cgtcttgccg atggcgggaa g    21

<210> SEQ ID NO 25
<211> LENGTH: 23
<212> TYPE: DNA
<213> ORGANISM: Artificial Sequence
<220> FEATURE:
<223> OTHER INFORMATION: Synthetic Sequence - Primer

<400> SEQUENCE: 25
cgtaagaccg gcaagcgctc cac    23

<210> SEQ ID NO 26
<211> LENGTH: 21
<212> TYPE: DNA
<213> ORGANISM: Artificial Sequence
<220> FEATURE:
<223> OTHER INFORMATION: Synthetic Sequence - Primer

<400> SEQUENCE: 26
cgtcttgccg atggcgggaa g    21

<210> SEQ ID NO 27
<211> LENGTH: 27
<212> TYPE: DNA
<213> ORGANISM: Artificial Sequence
<220> FEATURE:
<223> OTHER INFORMATION: Synthetic Sequence - Primer

<400> SEQUENCE: 27

```
aaggcggccg agcgcatggc cttcaac                                              27

<210> SEQ ID NO 28
<211> LENGTH: 17
<212> TYPE: DNA
<213> ORGANISM: Artificial Sequence
<220> FEATURE:
<223> OTHER INFORMATION: Synthetic Sequence - Primer

<400> SEQUENCE: 28
ccgcacgctc ttcaccc                                                         17

<210> SEQ ID NO 29
<211> LENGTH: 27
<212> TYPE: DNA
<213> ORGANISM: Artificial Sequence
<220> FEATURE:
<223> OTHER INFORMATION: Synthetic Sequence - Primer

<400> SEQUENCE: 29
cgtgcggccg agcgcatggc cttcaac                                              27

<210> SEQ ID NO 30
<211> LENGTH: 17
<212> TYPE: DNA
<213> ORGANISM: Artificial Sequence
<220> FEATURE:
<223> OTHER INFORMATION: Synthetic Sequence - Primer

<400> SEQUENCE: 30
ccgcacgctc ttcaccc                                                         17

<210> SEQ ID NO 31
<211> LENGTH: 24
<212> TYPE: DNA
<213> ORGANISM: Artificial Sequence
<220> FEATURE:
<223> OTHER INFORMATION: Synthetic Sequence - Primer

<400> SEQUENCE: 31
gaacccaaag gccgggtcct cctg                                                 24

<210> SEQ ID NO 32
<211> LENGTH: 24
<212> TYPE: DNA
<213> ORGANISM: Artificial Sequence
<220> FEATURE:
<223> OTHER INFORMATION: Synthetic Sequence - Primer

<400> SEQUENCE: 32
aaagagggaa agcatcgcct ccat                                                 24

<210> SEQ ID NO 33
<211> LENGTH: 24
<212> TYPE: DNA
<213> ORGANISM: Artificial Sequence
<220> FEATURE:
<223> OTHER INFORMATION: Synthetic Sequence - Primer

<400> SEQUENCE: 33
aagcccaaag gccgggtcct cctg                                                 24

<210> SEQ ID NO 34
<211> LENGTH: 24
<212> TYPE: DNA
```

```
<213> ORGANISM: Artificial Sequence
<220> FEATURE:
<223> OTHER INFORMATION: Synthetic Sequence - Primer

<400> SEQUENCE: 34
aaagagcgga agcatcgcct ccat                                          24

<210> SEQ ID NO 35
<211> LENGTH: 24
<212> TYPE: DNA
<213> ORGANISM: Artificial Sequence
<220> FEATURE:
<223> OTHER INFORMATION: Synthetic Sequence - Primer

<400> SEQUENCE: 35
aagcccaaag gccgggtcct cctg                                          24

<210> SEQ ID NO 36
<211> LENGTH: 24
<212> TYPE: DNA
<213> ORGANISM: Artificial Sequence
<220> FEATURE:
<223> OTHER INFORMATION: Synthetic Sequence - Primer

<400> SEQUENCE: 36
aaagagggaa agcatcgcct ccat                                          24

<210> SEQ ID NO 37
<211> LENGTH: 27
<212> TYPE: DNA
<213> ORGANISM: Artificial Sequence
<220> FEATURE:
<223> OTHER INFORMATION: Synthetic Sequence - Primer

<400> SEQUENCE: 37
aaggccctga aggaggacgg gtacaag                                       27

<210> SEQ ID NO 38
<211> LENGTH: 25
<212> TYPE: DNA
<213> ORGANISM: Artificial Sequence
<220> FEATURE:
<223> OTHER INFORMATION: Synthetic Sequence - Primer

<400> SEQUENCE: 38
gaggaggttc ttggcgaagc cgtag                                         25

<210> SEQ ID NO 39
<211> LENGTH: 36
<212> TYPE: DNA
<213> ORGANISM: Artificial Sequence
<220> FEATURE:
<223> OTHER INFORMATION: Synthetic Sequence - Primer

<400> SEQUENCE: 39
aaggccctgc aggacgacgg gtacaaggcc gtcttc                             36

<210> SEQ ID NO 40
<211> LENGTH: 25
<212> TYPE: DNA
<213> ORGANISM: Artificial Sequence
<220> FEATURE:
<223> OTHER INFORMATION: Synthetic Sequence - Primer

<400> SEQUENCE: 40
gaggaggctc ttggcgaagc cgtag                                         25
```

<210> SEQ ID NO 41
<211> LENGTH: 36
<212> TYPE: DNA
<213> ORGANISM: Artificial Sequence
<220> FEATURE:
<223> OTHER INFORMATION: Synthetic Sequence - Primer

<400> SEQUENCE: 41
aaggccctgc aggacgacgg gtacaaggcc gtcttc                                36

<210> SEQ ID NO 42
<211> LENGTH: 25
<212> TYPE: DNA
<213> ORGANISM: Artificial Sequence
<220> FEATURE:
<223> OTHER INFORMATION: Synthetic Sequence - Primer

<400> SEQUENCE: 42
gaggaggttc ttggcgaagc cgtag                                            25

<210> SEQ ID NO 43
<211> LENGTH: 24
<212> TYPE: DNA
<213> ORGANISM: Artificial Sequence
<220> FEATURE:
<223> OTHER INFORMATION: Synthetic Sequence - Primer

<400> SEQUENCE: 43
gacctcaggc tctccttgga gctc                                             24

<210> SEQ ID NO 44
<211> LENGTH: 24
<212> TYPE: DNA
<213> ORGANISM: Artificial Sequence
<220> FEATURE:
<223> OTHER INFORMATION: Synthetic Sequence - Primer

<400> SEQUENCE: 44
gttcaggtgg gccttgatct tctc                                             24

<210> SEQ ID NO 45
<211> LENGTH: 26
<212> TYPE: DNA
<213> ORGANISM: Artificial Sequence
<220> FEATURE:
<223> OTHER INFORMATION: Synthetic Sequence - Primer

<400> SEQUENCE: 45
aagaagacag gcaagcgctc caccag                                           26

<210> SEQ ID NO 46
<211> LENGTH: 21
<212> TYPE: DNA
<213> ORGANISM: Artificial Sequence
<220> FEATURE:
<223> OTHER INFORMATION: Synthetic Sequence - Primer

<400> SEQUENCE: 46
cgtcttcccc aaggcgggaa g                                                21

<210> SEQ ID NO 47
<211> LENGTH: 26
<212> TYPE: DNA
<213> ORGANISM: Artificial Sequence
<220> FEATURE:

<223> OTHER INFORMATION: Synthetic Sequence - Primer

<400> SEQUENCE: 47
cggaagacag gcaagcgctc caccag                      26

<210> SEQ ID NO 48
<211> LENGTH: 21
<212> TYPE: DNA
<213> ORGANISM: Artificial Sequence
<220> FEATURE:
<223> OTHER INFORMATION: Synthetic Sequence - Primer

<400> SEQUENCE: 48
cgtcttcccc aaggcgggaa g                           21

<210> SEQ ID NO 49
<211> LENGTH: 24
<212> TYPE: DNA
<213> ORGANISM: Artificial Sequence
<220> FEATURE:
<223> OTHER INFORMATION: Synthetic Sequence - Primer

<400> SEQUENCE: 49
aaggccgcgg agcgcatggc cttc                        24

<210> SEQ ID NO 50
<211> LENGTH: 25
<212> TYPE: DNA
<213> ORGANISM: Artificial Sequence
<220> FEATURE:
<223> OTHER INFORMATION: Synthetic Sequence - Primer

<400> SEQUENCE: 50
cctgacgctc ttcacccggg cgttg                       25

<210> SEQ ID NO 51
<211> LENGTH: 27
<212> TYPE: DNA
<213> ORGANISM: Artificial Sequence
<220> FEATURE:
<223> OTHER INFORMATION: Synthetic Sequence - Primer

<400> SEQUENCE: 51
ctgaagaccc tggaggaggg gaggaag                     27

<210> SEQ ID NO 52
<211> LENGTH: 24
<212> TYPE: DNA
<213> ORGANISM: Artificial Sequence
<220> FEATURE:
<223> OTHER INFORMATION: Synthetic Sequence - Primer

<400> SEQUENCE: 52
gagccaggcc cgcaccttgg ggag                        24

<210> SEQ ID NO 53
<211> LENGTH: 27
<212> TYPE: DNA
<213> ORGANISM: Artificial Sequence
<220> FEATURE:
<223> OTHER INFORMATION: Synthetic Sequence - Primer

<400> SEQUENCE: 53
gaaaagaccc tggaggaggg gaggaag                     27

-continued

```
<210> SEQ ID NO 54
<211> LENGTH: 24
<212> TYPE: DNA
<213> ORGANISM: Artificial Sequence
<220> FEATURE:
<223> OTHER INFORMATION: Synthetic Sequence - Primer

<400> SEQUENCE: 54
gagccaggcc cgcaccttgg ggag                                          24

<210> SEQ ID NO 55
<211> LENGTH: 27
<212> TYPE: DNA
<213> ORGANISM: Artificial Sequence
<220> FEATURE:
<223> OTHER INFORMATION: Synthetic Sequence - Primer

<400> SEQUENCE: 55
ctgaagaccc tggaggaggg gaggaag                                       27

<210> SEQ ID NO 56
<211> LENGTH: 24
<212> TYPE: DNA
<213> ORGANISM: Artificial Sequence
<220> FEATURE:
<223> OTHER INFORMATION: Synthetic Sequence - Primer

<400> SEQUENCE: 56
gagccaggcc cgcaccttgg ggag                                          24

<210> SEQ ID NO 57
<211> LENGTH: 27
<212> TYPE: DNA
<213> ORGANISM: Artificial Sequence
<220> FEATURE:
<223> OTHER INFORMATION: Synthetic Sequence - Primer

<400> SEQUENCE: 57
aagaagaccc tggaggaggg gaggaag                                       27

<210> SEQ ID NO 58
<211> LENGTH: 24
<212> TYPE: DNA
<213> ORGANISM: Artificial Sequence
<220> FEATURE:
<223> OTHER INFORMATION: Synthetic Sequence - Primer

<400> SEQUENCE: 58
gagccaggcc cgcaccttgg ggag                                          24

<210> SEQ ID NO 59
<211> LENGTH: 27
<212> TYPE: DNA
<213> ORGANISM: Artificial Sequence
<220> FEATURE:
<223> OTHER INFORMATION: Synthetic Sequence - Primer

<400> SEQUENCE: 59
ctcaagaccc tggaggaggg gaggaag                                       27

<210> SEQ ID NO 60
<211> LENGTH: 24
<212> TYPE: DNA
<213> ORGANISM: Artificial Sequence
<220> FEATURE:
<223> OTHER INFORMATION: Synthetic Sequence - Primer
```

<400> SEQUENCE: 60
gagccaggcc cgcaccttgg ggag                                              24

<210> SEQ ID NO 61
<211> LENGTH: 27
<212> TYPE: DNA
<213> ORGANISM: Artificial Sequence
<220> FEATURE:
<223> OTHER INFORMATION: Synthetic Sequence - Primer

<400> SEQUENCE: 61
ctgaagaccc tggaggaggg gaggaag                                           27

<210> SEQ ID NO 62
<211> LENGTH: 24
<212> TYPE: DNA
<213> ORGANISM: Artificial Sequence
<220> FEATURE:
<223> OTHER INFORMATION: Synthetic Sequence - Primer

<400> SEQUENCE: 62
tatccaggcc cgcaccttgg ggag                                              24

<210> SEQ ID NO 63
<211> LENGTH: 27
<212> TYPE: DNA
<213> ORGANISM: Artificial Sequence
<220> FEATURE:
<223> OTHER INFORMATION: Synthetic Sequence - Primer

<400> SEQUENCE: 63
aagaagaccc tggaggaggg gaggaag                                           27

<210> SEQ ID NO 64
<211> LENGTH: 24
<212> TYPE: DNA
<213> ORGANISM: Artificial Sequence
<220> FEATURE:
<223> OTHER INFORMATION: Synthetic Sequence - Primer

<400> SEQUENCE: 64
tatccaggcc cgcaccttgg ggag                                              24

<210> SEQ ID NO 65
<211> LENGTH: 27
<212> TYPE: DNA
<213> ORGANISM: Artificial Sequence
<220> FEATURE:
<223> OTHER INFORMATION: Synthetic Sequence - Primer

<400> SEQUENCE: 65
ctcaagaccc tggaggaggg gaggaag                                           27

<210> SEQ ID NO 66
<211> LENGTH: 24
<212> TYPE: DNA
<213> ORGANISM: Artificial Sequence
<220> FEATURE:
<223> OTHER INFORMATION: Synthetic Sequence - Primer

<400> SEQUENCE: 66
tatccaggcc cgcaccttgg ggag                                              24

<210> SEQ ID NO 67
<211> LENGTH: 24

```
<212> TYPE: DNA
<213> ORGANISM: Artificial Sequence
<220> FEATURE:
<223> OTHER INFORMATION: Synthetic Sequence - Primer

<400> SEQUENCE: 67
aaggccgcgg agcgcatggc cttc                                          24

<210> SEQ ID NO 68
<211> LENGTH: 25
<212> TYPE: DNA
<213> ORGANISM: Artificial Sequence
<220> FEATURE:
<223> OTHER INFORMATION: Synthetic Sequence - Primer

<400> SEQUENCE: 68
cctgacgctc ttcacccggg cgttg                                         25

<210> SEQ ID NO 69
<211> LENGTH: 24
<212> TYPE: DNA
<213> ORGANISM: Artificial Sequence
<220> FEATURE:
<223> OTHER INFORMATION: Synthetic Sequence - Primer

<400> SEQUENCE: 69
ccggccgcgg agcgcatggc cttc                                          24

<210> SEQ ID NO 70
<211> LENGTH: 25
<212> TYPE: DNA
<213> ORGANISM: Artificial Sequence
<220> FEATURE:
<223> OTHER INFORMATION: Synthetic Sequence - Primer

<400> SEQUENCE: 70
cctgacgctc ttcacccggg cgttg                                         25

<210> SEQ ID NO 71
<211> LENGTH: 27
<212> TYPE: DNA
<213> ORGANISM: Artificial Sequence
<220> FEATURE:
<223> OTHER INFORMATION: Synthetic Sequence - Primer

<400> SEQUENCE: 71
ggcgaggtgg cggctttggc caaggag                                       27

<210> SEQ ID NO 72
<211> LENGTH: 21
<212> TYPE: DNA
<213> ORGANISM: Artificial Sequence
<220> FEATURE:
<223> OTHER INFORMATION: Synthetic Sequence - Primer

<400> SEQUENCE: 72
ggcccgcgct tgggggggcct c                                            21

<210> SEQ ID NO 73
<211> LENGTH: 27
<212> TYPE: DNA
<213> ORGANISM: Artificial Sequence
<220> FEATURE:
<223> OTHER INFORMATION: Synthetic Sequence - Primer

<400> SEQUENCE: 73
```
ggcgccgtgg cggctttggc caaggag                                27

<210> SEQ ID NO 74
<211> LENGTH: 21
<212> TYPE: DNA
<213> ORGANISM: Artificial Sequence
<220> FEATURE:
<223> OTHER INFORMATION: Synthetic Sequence - Primer

<400> SEQUENCE: 74
ggcccgcgct tgggggcct c                                       21

<210> SEQ ID NO 75
<211> LENGTH: 25
<212> TYPE: DNA
<213> ORGANISM: Artificial Sequence
<220> FEATURE:
<223> OTHER INFORMATION: Synthetic Sequence - Primer

<400> SEQUENCE: 75
aagaaaaacc ggtaaacgta gcacc                                  25

<210> SEQ ID NO 76
<211> LENGTH: 24
<212> TYPE: DNA
<213> ORGANISM: Artificial Sequence
<220> FEATURE:
<223> OTHER INFORMATION: Synthetic Sequence - Primer

<400> SEQUENCE: 76
ggttttgccc agcgcaggca gacg                                   24

<210> SEQ ID NO 77
<211> LENGTH: 25
<212> TYPE: DNA
<213> ORGANISM: Artificial Sequence
<220> FEATURE:
<223> OTHER INFORMATION: Synthetic Sequence - Primer

<400> SEQUENCE: 77
ccgaaaaacc ggtaaacgta gcacc                                  25

<210> SEQ ID NO 78
<211> LENGTH: 24
<212> TYPE: DNA
<213> ORGANISM: Artificial Sequence
<220> FEATURE:
<223> OTHER INFORMATION: Synthetic Sequence - Primer

<400> SEQUENCE: 78
ggttttgccc agcgcaggca gacg                                   24

<210> SEQ ID NO 79
<211> LENGTH: 30
<212> TYPE: DNA
<213> ORGANISM: Artificial Sequence
<220> FEATURE:
<223> OTHER INFORMATION: Synthetic Sequence - Primer

<400> SEQUENCE: 79
aaggcagccg aacgtatggc ctttaatatg                             30

<210> SEQ ID NO 80
<211> LENGTH: 24
<212> TYPE: DNA
<213> ORGANISM: Artificial Sequence

```
<220> FEATURE:
<223> OTHER INFORMATION: Synthetic Sequence - Primer

<400> SEQUENCE: 80
acgaactgat ttaacacgtg catt                                          24

<210> SEQ ID NO 81
<211> LENGTH: 30
<212> TYPE: DNA
<213> ORGANISM: Artificial Sequence
<220> FEATURE:
<223> OTHER INFORMATION: Synthetic Sequence - Primer

<400> SEQUENCE: 81
ccggcagccg aacgtatggc ctttaatatg                                    30

<210> SEQ ID NO 82
<211> LENGTH: 24
<212> TYPE: DNA
<213> ORGANISM: Artificial Sequence
<220> FEATURE:
<223> OTHER INFORMATION: Synthetic Sequence - Primer

<400> SEQUENCE: 82
acgaactgat ttaacacgtg catt                                          24
```

MODIFIED HEAT-RESISTANT DNA POLYMERASE

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 41,401 byes ASCII (Text) file named "759754-Replacement_Sequence_Listing.txt," created Mar. 14, 2024.

TECHNICAL FIELD

The present invention relates to mutants of heat-resistant DNA polymerases for use in polymerase chain reaction (PCR) etc. The present invention further relates to a nucleic acid amplification method that uses the heat-resistant DNA polymerases. The present invention is applicable not only to research, but also clinical diagnosis, environmental testing, etc.

BACKGROUND ART

A nucleic acid amplification method is a technique for amplifying a few copies of target nucleic acid to a visible level, i.e., to hundreds of millions of copies or more, and is widely used not only in the field of life science research, but also in medical fields, such as genetic diagnosis and clinical testing, as well as microorganism testing etc. in foods or the environment.

A typical nucleic acid amplification method is PCR (Polymerase Chain Reaction). PCR is a method for amplification of target nucleic acid in a sample by repeating a cycle consisting of three steps: (1) DNA denaturation by heat treatment (dissociation from double-stranded DNA to single-stranded DNA), (2) annealing of primers to the single-stranded DNA template, and (3) extension of the primers by DNA polymerase.

RT-PCR, in which RNA is converted to cDNA with a reverse transcriptase (reverse transcription reaction) before performing PCR, is also widely used when a target nucleic acid to be detected is RNA, for example, when a target to be detected in pathogenic microorganism detection is an RNA virus; when the amount of gene expression is measured by mRNA quantification; or the like.

These nucleic acid amplification methods are known to be strongly inhibited by inhibitors, such as sugars and proteins present in biological samples, causing a reduction in amplification efficiency and detection sensitivity. Thus, before the nucleic acid amplification described above, extraction of nucleic acid from biological samples and purification are required.

A known method for nucleic acid extraction from a biological sample uses an organic solvent, such as phenol and chloroform (Patent Literature (PTL) 1). However, even if nucleic acid in a sample is purified by using such a method, complete removal of contaminants is difficult. Further, the amount of nucleic acid recovered from samples often varies. In particular, when a sample contains a small amount of nucleic acid, performing nucleic acid amplification can be difficult.

Another one of the problems in nucleic acid amplification methods is that the reaction is time-consuming. PCR reaction generally requires adjustment of extension time according to the size of target nucleic acid; the extension time is usually set to be about 1 minute per 1 kb. When the target is a long nucleic acid, the reaction time can exceed 2 to 3 hours. Additionally, the reaction for reverse transcription usually requires about 20 minutes.

Due to the above, further improvement in the reaction system has been in demand, requiring nucleic acid amplification methods that achieve stronger resistance to inhibitors, and that can perform the reaction within a shorter period of time.

In fact, to increase reaction efficiency, improvement in DNA polymerase has been considered (PTL 2, PTL 3, and PTL 4, and Non-Patent Literature (NPL) 1, NPL 2, and NPL 3). PTL 2 succeeded in obtaining a modified DNA polymerase that is resistant to inhibition by salts etc. by introducing mutations in Taq DNA polymerase, which is usually used in PCR. Likewise, PTL 3, NPL 1, NPL 2, and NPL 3 also disclose obtaining a modified DNA polymerase that is resistant to blood or inhibition, by introducing mutations in Taq DNA polymerase.

However, the production of such mutants has been performed only with respect to most widely used Taq DNA polymerase, and mutations in other DNA polymerases have not been performed. Further, although these documents disclose examples of achieving better resistance to inhibition by contaminants, shortening the reaction time is nowhere mentioned.

Taq DNA polymerase, which has poor reverse transcription activity, cannot be used in RT-PCR. Further, many examples demonstrating that the use of mutants of Taq DNA polymerase is also insufficient to efficiently perform the reaction have been found in various documents. Accordingly, DNA polymerases with higher performance have been in demand.

CITATION LIST

Patent Literature

PTL 1: JPH09-19292A
PTL 2: JP5809059B
PTL 3: JP5852650B
PTL 4: JP5189101B

Non-Patent Literature

NPL 1: Original Research Article (published on Aug. 14, 2014)
NPL 2: Nucleic Acids Research, Vol. 37, No. 5 e40 (published in 2009)
NPL 3: Original Research Article (published in Sep. 3, 2014)

SUMMARY OF INVENTION

Technical Problem

DNA polymerases have been required that are highly resistant to inhibitors and that can shorten the PCR reaction time in nucleic acid amplification methods, in particular, in PCR or RT-PCR.

Solution to Problem

In view of the above problems, the present inventors conducted extensive research, and consequently found that the introduction of a mutation or mutations in a DNA polymerase that has reverse transcription activity achieves a higher resistance to inhibitors and enables considerable shortening of the reaction time, compared to existing Taq DNA polymerase or Taq DNA polymerase mutants comprising a mutation or mutations at the same site(s). The present inventors also found that since DNA polymerases that have reverse transcription activity are used, the resulting modified DNA polymerases are applicable even to RT-PCR, which was previously impossible. The present invention has thus been accomplished.

More specifically, the present invention is summarized below.

Item 1. A DNA polymerase having reverse transcription activity and having 90% or more identity to the amino acid sequence of SEQ ID NO: 1, wherein the DNA polymerase comprises an amino acid modification at at least one position selected from the group consisting of position 509 and position 744.

Item 2. A DNA polymerase having reverse transcription activity and having 96% or more identity to the amino acid sequence of SEQ ID NO: 1, wherein the DNA polymerase comprises an amino acid modification at at least one position selected from the group consisting of position 509 and position 744.

Item 3. A DNA polymerase having reverse transcription activity and having the amino acid sequence of SEQ ID NO: 1, wherein the DNA polymerase comprises an amino acid modification at at least one position selected from the group consisting of position 509 and position 744.

Item 4. A DNA polymerase having reverse transcription activity and having 90% or more identity to the amino acid sequence of SEQ ID NO: 2, wherein the DNA polymerase comprises an amino acid modification at at least one position selected from the group consisting of position 509 and position 744.

Item 5. A DNA polymerase having reverse transcription activity and having 96% or more identity to the amino acid sequence of SEQ ID NO: 2, wherein the DNA polymerase comprises an amino acid modification at at least one position selected from the group consisting of position 509 and position 744.

Item 6. A DNA polymerase having reverse transcription activity and having the amino acid sequence of SEQ ID NO: 2, wherein the DNA polymerase comprises an amino acid modification at at least one position selected from the group consisting of position 509 and position 744.

Item 7. The DNA polymerase according to any one of Items 1 to 6, wherein the amino acid modification at position 509 or 744 of SEQ ID NO: 1 or SEQ ID NO: 2 is substitution with an amino acid selected from the group consisting of histidine, lysine, and arginine.

Item 8. The DNA polymerase according to Item 7, wherein the amino acid modification at position 509 of SEQ ID NO: 1 or SEQ ID NO: 2 is substitution with arginine.

Item 9. The DNA polymerase according to any one of Items 1 to 8, with which a reverse transcription reaction is completed in 5 minutes or less.

Item 10. The DNA polymerase according to Item 9, with which a reverse transcription reaction is completed in 1 minute or less.

Item 11. The DNA polymerase according to any one of Items 1 to 10, wherein the extension time per kb is 30 seconds or less.

Item 12. A nucleic acid amplification method comprising amplifying a biological sample that is not purified, using the DNA polymerase of any one of Items 1 to 11.

Item 13. The nucleic acid amplification method according to Item 12, wherein the biological sample is at least one sample selected from the group consisting of blood-derived samples, saliva, cerebrospinal fluid, urine, and milk.

Advantageous Effects of Invention

The use of the DNA polymerases of the present invention enables nucleic acid amplification to be performed within a short reaction time, without being affected by contaminants. Since the purification step of removing contaminants can be omitted, the processing time can be considerably shortened.

DESCRIPTION OF EMBODIMENTS

Figure 1:
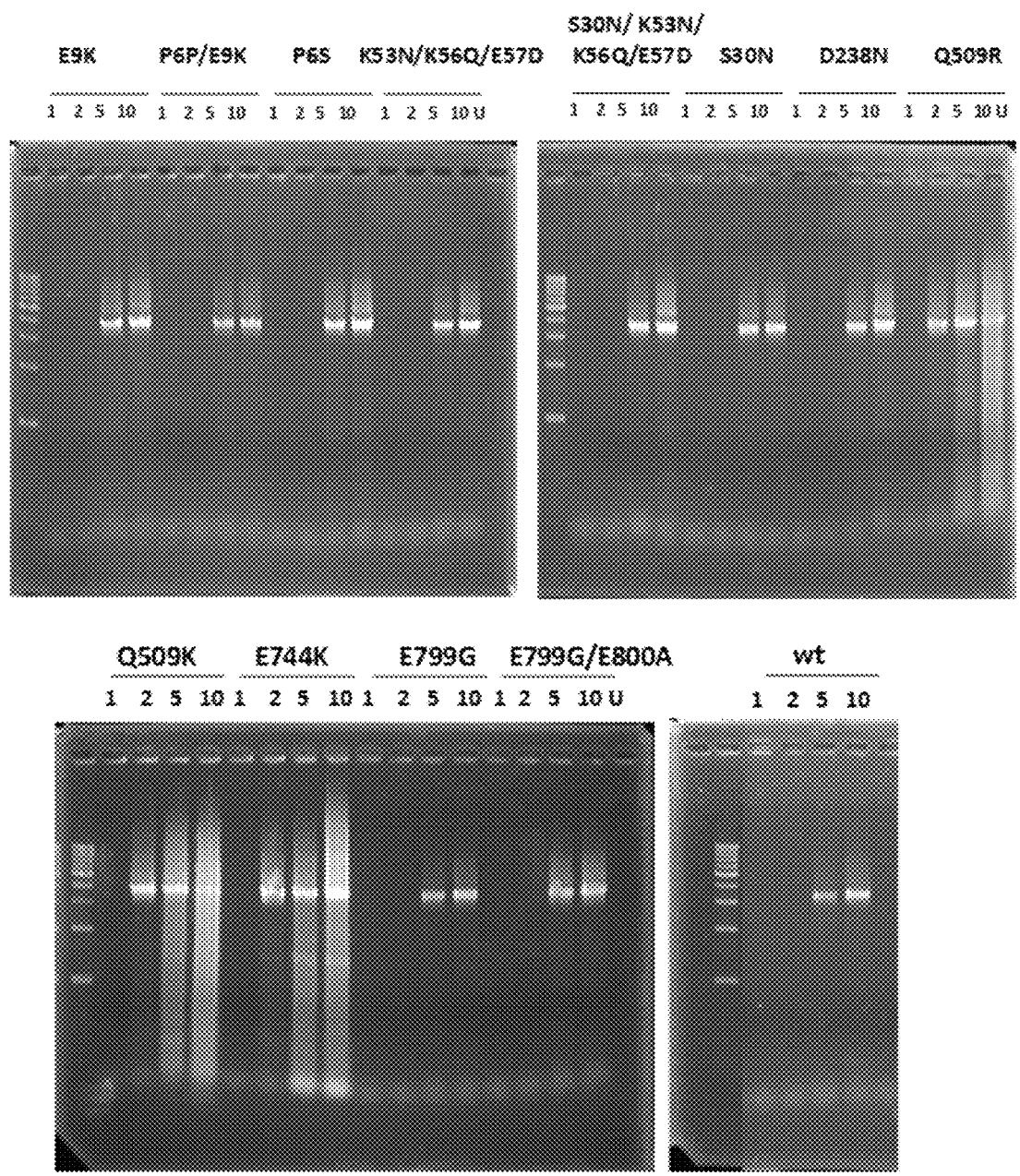
FIG. 1 shows the analytical results of DNA amplification using Tth DNA polymerase and modified Tth DNA polymerases in Example 3.

The present invention relates to modified DNA polymerases that have reverse transcription activity. A heat-resistant DNA polymerase that has reverse transcription activity refers to a DNA polymerase that has both an ability to convert RNA to cDNA, and an ability to amplify DNA. Without intending to particularly limit the present invention, examples include a DNA polymerase from *Thermus thermophilus* HB8 (Tth), a DNA polymerase from *Thermus* sp. Z05 (Z05), a DNA polymerase from *Thermotoga maritima* (Tma), and the like, with Tth and Z05 being particularly preferable.

The DNA polymerase according to the present invention is characterized in that at least one amino acid at a specific position is mutated, i.e., modified by being substituted with another amino acid, in a protein having the amino acid sequence of SEQ ID NO: 1. The amino acid sequence before modification is not limited to be completely the same as that of SEQ ID NO: 1. The amino acid sequence before modification may have 80% or more, preferably 85% or more, more preferably 90% or more, still more preferably 93% or more, and particularly preferably 96% or more, identity to the amino acid sequence of SEQ ID NO: 1.

The DNA polymerase according to the present invention more preferably comprises a modification of at least one amino acid selected from amino acids corresponding to Q509 and E744 in SEQ ID NO: 1 or SEQ ID NO: 2. Here, for example, Q509 refers to the amino acid at position 509, i.e., a glutamine (Q) residue. The single alphabetical letters represent commonly used amino acid abbreviations. In a preferable example, Q509 amino acid, i.e., glutamine (Q), is substituted with a positively charged, polar amino acid; more specifically, the amino acid substitution is selected from the group consisting of Q509H, Q509K, and Q509R. Here, Q509K, for example, represents the amino acid at position 509, i.e., glutamine (Q), being substituted with lysine (K); the same applies hereinafter. In another preferable example, E744 amino acid, glutamic acid (E), is substituted with a positively charged, polar amino acid; more specifically, the amino acid substitution is E744H, E744K, or E744R.

In the DNA polymerase according to the present invention, either of the amino acids at position 509 or 744 in SEQ ID NO: 1 or SEQ ID NO: 2 is modified, and other amino acids may be optionally deleted or modified. Specifically, the N-terminus may be deleted to remove 5'-3' exonuclease activity, or a mutation, such as E710L, may be introduced to stop reactions at low temperatures; however, there is no particular limitation. It is possible that the DNA polymerase according to the present invention comprises mutations at any sites in addition to position 509 or 744. The DNA polymerase preferably comprises a mutation at position 509 or 744, and has 90% or more sequence identity to SEQ ID NO: 1 or 2, and more preferably has 96% or more sequence identity to SEQ ID NO: 1 or 2.

Such modified DNA polymerases may be produced by hitherto-known methods. For examples, a preferable production method comprises introducing one or more mutations into a gene encoding a wild-type DNA polymerase, and producing a mutated (modified) DNA polymerase with a new function by protein engineering techniques.

In one embodiment, the method for introducing amino acid modifications may be inverse PCR-based site-directed mutagenesis. For example, a KOD-Plus-Mutagenesis Kit (produced by Toyobo Co. Ltd.) is a kit to obtain a transformant carrying a plasmid into which a desired mutation is introduced, by the following: (1) denaturing a plasmid into which a target gene is inserted, annealing mutant primers to the plasmid, and subsequently performing an extension reaction with a KOD DNA polymerase; (2) repeating the cycle of (1) 15 times; (3) selectively cleaving only the plasmid as a template with restriction enzyme DpnI; (4) circularizing the newly synthesized gene by phosphorylation and ligation; and (5) transforming the circularized gene into *Escherichia coli*.

The DNA polymerase according to the present invention may be in the form of a fused protein with a protein, such as Sso7d and PCNA; or may be a fused protein with a protein tag, such as an His-tag and a GST tag.

In another embodiment, the DNA polymerase according to the present invention preferably has more excellent reverse transcription activity than hitherto-known DNA polymerases, and enables a reverse transcription reaction to proceed more quickly. In a specific embodiment, for example, the reverse transcription reaction is completed in 5 minutes or less, preferably 3 minutes or less, and more preferably 1 minute or less. In the present invention, the completion of the reverse transcription reaction is defined as follows. Specifically, the RT-PCR reaction is considered to be completed when the PCR efficiency is 90 to 110%, and correlation coefficient $r^2$ is 0.98. The PCR efficiency is calculated using Formula (1) below, based on the slope of the calibration curve plotting the results while setting the X axis as the amounts of serially diluted nucleic acid and the Y axis as the Ct values corresponding to the amounts of nucleic acid. Correlation coefficient $r^2$ represents the linearity of calibration curve. In this manner, when it is in a state where PCR can be performed after the reverse transcription reaction, the reverse transcription reaction is considered to be completed.

$$\text{PCR efficiency (\%)} = (10^{-1/Slope} - 1) \times 100$$

The DNA polymerase gene is, if necessary, transferred to an expression vector; afterward, *Escherichia coli*, for example, as a host is transformed with the expression vector, and then applied to an agar medium containing a drug such as ampicillin to form colonies. The colonies are inoculated into a nutrient medium, for example, an LB medium or a 2×YT medium, and cultured at 37° C. for 12 to 20 hours. Thereafter, the bacterial cells are disrupted to extract a crude enzyme solution. The vector is preferably derived from pBluescript. As a method for disrupting the cells, any known technique may be used. For example, sonication, French press disruption, glass bead disruption, and like physical disruption methods; and lytic enzymes such as lysozyme are usable. This crude enzyme solution is heat-treated at 80° C. for 30 minutes to deactivate the DNA polymerase derived from the host, and DNA polymerase activity is measured.

As a method for obtaining a purified DNA polymerase from the strain selected by the above-mentioned method, any technique may be used. Examples of the method include the following. The bacterial cells obtained after culturing on the nutrient medium are collected and disrupted by an enzymatic or physical disruption method to extract a crude enzyme solution. A DNA polymerase fraction is collected from the obtained crude enzyme extract by performing heat treatment, for example, at 80° C. for 30 minutes, followed by ammonium sulfate precipitation. This crude enzyme solution can be desalted by a method such as gel filtration with Sephadex G-25 (produced by Amersham Pharmacia Biotech). After this operation, separation and purification are performed by heparin-Sepharose column chromatography to obtain a purified enzyme sample. The purified enzyme sample is purified to such an extent that the sample shows a nearly single band in SDS-PAGE.

Method for Measuring DNA Polymerase Activity

The activity of purified DNA polymerase can be measured by the following method. If the enzyme activity in a sample is high, activity measurement is carried out after the sample is diluted with a storage buffer (50 mM Tris-HCl (pH 8.0), 50 mM KCl, 1 mM dithiothreitol, 0.1% Tween20, 0.1% Nonidet P40, 50% glycerin). (1) To a microtube, 25 µl of Solution A shown below, 5 µl of Solution B shown below, 5 µl of Solution C shown below, 10 µl of sterile water, and 5 µl of an enzyme solution are added, and reacted at 75° C. for 10 minutes. (2) Thereafter, the resulting mixture is ice-cooled, 50 µl of Solution E and 100 µl of Solution D are added thereto, and the mixture is stirred, followed by further ice-cooling for 10 minutes. (3) The solution is filtered through a glass filter (GF/C filter, produced by Whatman), and the filter is washed sufficiently with 0.1 N hydrochloric acid and ethanol. (4) The radioactivity of the filter is measured with a liquid scintillation counter (Tri-Carb 2810 TR, produced by Packard) to determine the incorporation of nucleotides into the template DNA. One unit of enzyme activity is defined as the amount of enzyme that catalyzes the incorporation of 10 nmol of nucleotides into an acid-insoluble fraction (i.e., a fraction that becomes insoluble when Solution D is added) per 30 minutes under the above conditions.

A: 40 mM Tris-HCl buffer (pH 7.5), 16 mM magnesium chloride, 15 mM dithiothreitol, 100 µg/ml BSA (bovine serum albumin)

B: 1.5 µg/µl activated calf thymus DNA
C: 1.5 mM dNTP (250 cpm/pmol [3H]dTTP)
D: 20% trichloroacetic acid (2 mM sodium pyrophosphate)
E: 1 mg/ml calf thymus DNA In the nucleic acid amplification method according to the present invention, although the conditions for nucleic acid amplification, such as temperature, time, and reaction cycles, vary according to the type, base sequence, chain length, etc., of the nucleic acid to be amplified, a person skilled in the art can suitably determine the conditions. However, when the nucleic acid amplification method according to the present invention is used, in particular, for PCR or RT-PCR, the extension time per kb may be adjusted to be 30 seconds or less. In PCR or RT-PCR, a cycle consisting of the following 3 steps is repeated: (1) DNA denaturation by heat treatment (dissociation from double-stranded DNA to single-stranded DNA), (2) annealing of primers to the single-stranded DNA template, and (3) extension of the primers by DNA polymerase. In the present invention, the extension time refers to the time required for a primer extension reaction in (3) per cycle.

Purification Process not Required

In the nucleic acid amplification method according to the present invention, nucleic acids in biological samples that are not purified can be amplified without performing purification. The term "purification" as used herein refers to a method for separating contaminants, such as tissues and cell walls of a biological sample, from DNA in the biological sample. Specific examples include a method for separating DNA using phenol, phenol/chloroform, or the like; a method for separating DNA using an ion-exchange resin, glass filter, or a reagent having protein aggregation action; and the like.

The nucleic acid amplification method according to the present invention is a method for performing amplification by adding a biological sample to a nucleic acid amplification reaction solution, without involving any of the above purification methods. In the present invention, "a biological sample that is not purified" refers to, for example, a biological sample itself; a sample obtained by diluting a liquid biological sample with a solvent, such as water or a nucleic acid storage solution; a sample obtained by adding a biological sample to a solvent, such as water, and heating to cause disruption; or a sample adhering to a substance containing a nucleic acid storage solution, such as FTA cards (GE Healthcare).

When a nucleic acid to be amplified is present within the tissue of a sample, such as an organ and a cell, the action of destroying the tissue for the purpose of extracting the nucleic acid (e.g., destroying by physical treatment or destroying using a surfactant etc.) does not correspond to purification in the present invention. Further, the action of diluting the sample or biological sample obtained through the above method with a buffer or the like also does not correspond to purification in the present invention.

Biological Sample

The biological sample to be applied to the nucleic acid amplification method of the present invention is not particularly limited, as long as it is obtained from a living body. Examples include tissues of animals or plants, body fluids, excrement, cells, bacteria, viruses, and the like. The body fluids include, but are not limited to, blood and saliva; and the cells include, but are not limited to, leukocytes separated from blood.

In addition to PCR and RT-PCR, the present invention can also be used in methods for synthesizing a DNA primer extension product, the method comprising reacting one primer with deoxyribonucleotide triphosphates (dNTPs), using DNA as a template to extend the primer. More specifically, the present invention can also be applied to methods, such as primer extension, sequencing, methods in which hitherto-known temperature cycling is not performed, and cycle sequencing.

The modified DNA polymerase of the present invention may be provided in the form of a reagent for nucleic acid amplification. In a preferable embodiment, examples of reagents for nucleic acid amplification include a reagent containing two primers, one of which is complementary to a DNA extension product of the other primer, dNTPs, the heat-resistant DNA polymerase of the present invention described above, a divalent ion, a monovalent ion, and a buffer; and specific examples include a reagent containing two primers, one of which is complementary to a DNA extension product of the other primer, dNTPs, the heat-resistant DNA polymerase, magnesium ion and/or manganese ion, ammonium ion and/or potassium ion, BSA, a nonionic surfactant described above, and a buffer.

In another embodiment, the reagent for nucleic acid amplification contains two primers, one of which is complementary to a DNA extension product of the other primer, dNTPs, the heat-resistant DNA polymerase of the present invention as described above, a divalent ion, a monovalent ion, and a buffer, and optionally an antibody having activity that reduces polymerase activity of the heat-resistant DNA polymerase and/or 5'-3' exonuclease activity of the heat-resistant DNA polymerase. Examples of the antibodies include monoclonal antibodies, polyclonal antibodies, and the like. These reagents for nucleic acid amplification are effective, in particular, in increasing PCR sensitivity and reducing nonspecific amplification.

The present invention is described below in more detail with reference to Examples. However, the present invention is not particularly limited to the Examples.

EXAMPLE

Example 1

Production of DNA Polymerase Plasmid

An artificially synthesized DNA polymerase gene from *Thermus thermophilus* HB8 (SEQ ID NO: 3), DNA polymerase gene from *Thermus* sp. Z05 (SEQ ID NO: 4), and heat-resistant DNA polymerase gene from *Thermus aquaticus* (SEQ ID NO: 5) were cloned into pBluescript to produce plasmids into which wild-type Tth, Z05, and Taq DNA polymerase were inserted (pTth, pZ05, and pTaq, respectively). To produce mutated plasmids, a KOD-Plus-Mutagenesis Kit (produced by Toyobo Co. Ltd.) was used in accordance with the instruction manual, using pTth, pZ05, or pTaq as a template. Double mutations were partly constructed using the produced mutated plasmids as a template by introducing further mutations using the same kit. Table 1 shows the produced plasmid, and the template and primers used during the production. *Escherichia coli* JM109 was transformed with the obtained plasmid, and used for enzyme preparation.

TABLE 1

| | Mutation site | Template | Primer | SEQ ID NO |
|---|---|---|---|---|
| pTaq | E507K | pTaq | aagaagaccggcaagcgctccac | 23 |
| | | | cgtcttgccgatggcgggaag | 24 |
| | E507R | pTaq | cgtaagaccggcaagcgctccac | 25 |
| | | | cgtcttgccgatggcgggaag | 26 |
| | E742K | pTaq | aaggcggccgagcgcatggccttcaac | 27 |
| | | | ccgcacgctcttcaccc | 28 |
| | E742R | pTaq | cgtgcggccgagcgcatggccttcaac | 29 |
| | | | ccgcacgctcttcaccc | 30 |
| pTth | P6S | pTth | gaacccaaaggccgggtcctcctg | 31 |
| | | | aaagagggaaagcatcgcctccat | 32 |
| | E9K | pTth | aagcccaaaggccgggtcctcctg | 33 |
| | | | aaagagcggaagcatcgcctccat | 34 |
| | P6S/E9K | pTth | aagcccaaaggccgggtcctcctg | 35 |
| | | | aaagagggaaagcatcgcctccat | 36 |
| | S30N | pTth | aaggccctgaaggaggacgggtacaag | 37 |
| | | | gaggaggttcttggcgaagccgtag | 38 |
| | K53N/K56Q/E57D | pTth | aaggccctgcaggacgacgggtacaaggccgtcttc | 39 |
| | | | gaggaggctcttggcgaagccgtag | 40 |
| | S30N/K53N/K56Q/E57D | pTth | aaggccctgcaggacgacgggtacaaggccgtcttc | 41 |
| | | | gaggaggttcttggcgaagccgtag | 42 |
| | D238N | pTth | gacctcaggctctccttggagctc | 43 |
| | | | gttcaggtgggccttgatcttctc | 44 |
| | Q509K | pTth | aagaagacaggcaagcgctccaccag | 45 |
| | | | cgtcttccccaaggcgggaag | 46 |
| | Q509R | pTth | cggaagacaggcaagcgctccaccag | 47 |
| | | | cgtcttccccaaggcgggaag | 48 |
| | Q509K/E744K | pTth | aaggccgcggagcgcatggccttc | 49 |
| | | Q509K | cctgacgctcttcacccgggcgttg | 50 |
| | Q509K/I709L/E710L | pTth | ctgaagaccctggaggaggggaggaag | 51 |
| | | Q509K | gagccaggcccgcaccttggggag | 52 |
| | I709L | pTth | gaaaagaccctggaggaggggaggaag | 53 |
| | | | gagccaggcccgcaccttggggag | 54 |
| | I709L/E710L | pTth | ctgaagaccctggaggaggggaggaag | 55 |
| | | | gagccaggcccgcaccttggggag | 56 |
| | I709L/E710K | pTth | aagaagaccctggaggaggggaggaag | 57 |
| | | | gagccaggcccgcaccttggggag | 58 |
| | I709L/E710Q | pTth | ctcaagaccctggaggaggggaggaag | 59 |
| | | | gagccaggcccgcaccttggggag | 60 |
| | E710L | pTth | ctgaagaccctggaggaggggaggaag | 61 |
| | | | tatccaggcccgcaccttggggag | 62 |
| | E710K | pTth | aagaagaccctggaggaggggaggaag | 63 |
| | | | tatccaggcccgcaccttggggag | 64 |
| | E710Q | pTth | ctcaagaccctggaggaggggaggaag | 65 |
| | | | tatccaggcccgcaccttggggag | 66 |
| | E744K | pTth | aaggccgcggagcgcatggccttc | 67 |
| | | | cctgacgctcttcacccgggcgttg | 68 |
| | E744R | pTth | ccggccgcggagcgcatggccttc | 69 |
| | | | cctgacgctcttcacccgggcgttg | 70 |
| | E799G | pTth | ggcgaggtggcggctttggccaaggag | 71 |
| | | | ggcccgcgcttggggggcctc | 72 |
| | E799G/E800A | pTth | ggcgccgtggcggctttggccaaggag | 73 |
| | | | ggcccgcgcttggggggcctc | 74 |
| pZ05 | Q509K | pZ05 | aagaaaaaccggtaaacgtagcacc | 75 |
| | | | ggttttgcccagcgcaggcagacg | 76 |
| | Q509R | pZ05 | ccgaaaaaccggtaaacgtagcacc | 77 |
| | | | ggttttgcccagcgcaggcagacg | 78 |
| | E744K | pZ05 | aaggcagccgaacgtatggcctttaatatg | 79 |
| | | | acgaactgatttaacacgtgcatt | 80 |
| | E744R | pZ05 | ccggcagccgaacgtatggcctttaatatg | 81 |
| | | | acgaactgatttaacacgtgcatt | 82 |

Example 2

Production of DNA Polymerase

The bacterial cells obtained in Example 1 were cultured as follows. First, 80 mL of a sterilized TB medium containing 100 μg/ml of ampicillin (Molecular Cloning, second edition, p. A2) was dispensed into a 500-mL Sakaguchi flask. Into this medium, *Escherichia coli* JM109 (strain transformed with the plasmid) (using a test tube) previously cultured at 37° C. for 16 hours in 3 ml of an LB medium containing 100 μg/ml of ampicillin (1% Bacto-tryptone, 0.5% yeast extract, 0.5% sodium chloride; produced by Gibco) was inoculated, and an aeration culture was conducted at 37° C. for 16 hours. The bacterial cells were collected from the culture medium by centrifugation, suspended in 50 ml of a disruption buffer (30 mM Tris-HCl buffer (pH 8.0), 30 mM NaCl, 0.1 mM EDTA), and then disrupted by sonication, thus obtaining a cell disruption solution. Subsequently, the cell disruption solution was treated at 80° C. for 15 minutes, after which the insoluble fraction was removed by centrifugation. Nucleic acid removal using polyethyleneimine, ammonium sulfate precipitation, and heparin-Sepharose chromatography were then carried out. Finally, replacement by a storage buffer (50 mM Tris-HCl buffer (pH 8.0), 50 mM potassium chloride, 1 mM dithiothreitol, 0.1% Tween 20, 0.1% Nonidet P40, 50% glycerin) was carried out. A heat-resistant DNA polymerase was thereby obtained.

The activity of the thus-purified DNA polymerase was measured in the manner as described below. When the enzyme activity was high, the sample was measured after dilution.

Reagent
  Solution A: 40 mM Tris-HCl buffer (pH 7.5), 16 mM magnesium chloride, 15 mM dithiothreitol, 100 µg/ml BSA
  Solution B: 1.5 µg/µl activated calf thymus DNA
  Solution C: 1.5 mM dNTP (250 cpm/pmol [3H]dTTP)
  Solution D: 20% trichloroacetic acid (2 mM sodium pyrophosphate)
  Solution E: 1 mg/ml calf thymus DNA Method To a microtube, 25 µl of Solution A, 5 µl of Solution B, 5 µl of Solution C, and 10 µl of sterile water were added, and the mixture was stirred. Thereafter, 5 µl of the purified enzyme diluted solution was added thereto, and reacted at 75° C. for 10 minutes. The resulting mixture was then cooled, 50 µl of Solution E and 100 µl of Solution D were added thereto, and the mixture was stirred, followed by further ice-cooling for 10 minutes. The solution was filtered through a glass filter (GF/C filter produced by Whatman), and the filter was washed sufficiently with 0.1 N hydrochloric acid and ethanol. The radioactivity of the filter was measured with a liquid scintillation counter (Tri-Carb2810 TR produced by Packard) to determine the incorporation of nucleotides into the template DNA. One unit of enzyme activity was defined as the amount of enzyme that catalyzes the incorporation of 10 nmol of nucleotides into an acid-insoluble fraction per 30 minutes under the above conditions.

Example 3

PCR

PCR was conducted to amplify 3.6 kb and 8.5 kb of human β-globin using the DNA polymerase produced in Example 2.

For PCR, the buffer provided with KOD Dash (produced by Toyobo Co. Ltd.) was used, and 50 µl of a reaction solution containing 1×PCR buffer, 0.2 mM dNTPs, 15 pmol of primers for amplifying 3.6 kb of human β-globin (SEQ ID NOs: 6 and 7) or 15 pmol of primers for amplifying 8.5 kb (SEQ ID NOs: 8 and 9), 50 ng of human genomic DNA (produced by Roche), and 1, 2, 5, or 10 U of enzyme was subjected to preliminary reaction at 94° C. for 2 minutes. Thereafter, PCR was performed using a GeneAmp PCR System 9700 (Applied Biosystems) by repeating a cycle 35 times, each cycle consisting of 10 seconds at 98° C., 10 seconds at 60° C., and 4 minutes (for 3.6 kb amplification) or 8 minutes (for 8.5 kb amplification) at 68° C. After completion of the reaction, 5 µl of each of the resulting reaction solutions was subjected to one percent agarose gel electrophoresis, followed by ethidium bromide staining to confirm the amount of amplified DNA fragments under ultraviolet irradiation.

FIG. 1 shows the results of amplification of 3.6 kb with the use of Tth DNA polymerase and modified Tth DNA polymerases (E9K, P6S/E9K, P6S, K53N/K56Q/E57D, S30N/K53N/K56Q/E57D, S30N, D238N, Q509R, Q509K, E744K, E799G, E799G/E800A). Amplification of these polymerases was performed for 1, 2, 5, and 10 U, and bands were detected for 5 U and 10 U. Q509R, Q509K, and E744K allowed amplification for even 2 U, which revealed that efficient amplification was possible with a smaller enzyme amount.

Tables 2 and 3 collectively show the results of amplification of 3.6 kb (Table 2) and 8.5 kb (Table 3) with the use of various DNA polymerases and mutants. ○ signifies that amplification was observed. Δ signifies that although amplification was observed, many bands were thin or nonspecific. X signifies that amplification was not observed.

The results revealed that E507K, E507R, E742K, and E742R mutants of Taq DNA polymerase achieved an increase in the amplification success rate, indicating that amplification of 3.6 kb was possible. Positions 507 and 742 respectively correspond to positons 509 and 744 in Tth and Z05; Tth and Z05 also showed improved performance when mutations were introduced at these positions. However, Taq DNA polymerase or the mutants thereof did not allow amplification of 8.5 kb. In contrast, Q509K, Q509R, E744K, and E744R mutants of Tth or Z05 that shows reverse transcription ability were confirmed to allow even amplification of 8.5 kb. The results clarified that DNA polymerases that show reverse transcription ability had higher performance, and that mutation introduction led to even higher performance. Although the mutation sites here have already been reported in terms of Taq DNA polymerase, many of these mutations in Tth DNA polymerase did not show the effect.

TABLE 2

| | Amplification or 3.6 kb | Enzyme amount (U) | | | |
|---|---|---|---|---|---|
| | | 1 | 2 | 5 | 10 |
| Taq | WT | x | x | x | x |
| | E507K | x | o | o | o |
| | E507R | x | o | o | o |
| | E742K | x | o | o | o |
| | E742R | x | o | o | o |
| Tth | WT | x | x | o | o |
| | P6S | x | x | o | o |
| | E9K | x | x | o | o |
| | P6S/E9K | x | x | o | o |
| | S30N | x | x | Δ | Δ |
| | K53N/K56Q/E57D | x | x | Δ | Δ |
| | S30N/K53N/K56Q/E57D | x | x | Δ | Δ |
| | D238N | x | x | Δ | Δ |
| | Q509K | x | o | o | o |
| | Q509R | x | o | o | o |
| | Q509K/E744K | x | x | o | o |
| | Q509K/I709L/E710L | x | x | o | o |
| | I709L | x | x | x | x |
| | I709L/E710L | x | x | x | x |
| | I709L/E710K | x | x | x | x |
| | I709L/E710Q | x | x | x | x |
| | E710L | x | x | o | o |
| | E710K | x | x | Δ | Δ |
| | E710Q | x | x | o | o |
| | E744K | x | o | o | o |
| | E744R | x | o | o | o |
| | E799G | x | x | o | o |
| | E799G/E800A | x | x | o | o |
| Z05 | WT | x | x | o | o |
| | Q509K | x | o | o | o |
| | Q509R | x | o | o | o |
| | E744K | x | o | o | o |
| | E744R | x | o | o | o |

TABLE 3

| Amplification of 8.5 kb | | Enzyme amount (U) | | | |
|---|---|---|---|---|---|
| | | 1 | 2 | 5 | 10 |
| Taq | WT | x | x | x | x |
| | E507K | x | x | x | x |
| | E507R | x | x | x | x |
| | E742K | x | x | x | x |
| | E742R | x | x | x | x |
| Tth | WT | x | x | x | x |
| | P6S | x | x | x | x |
| | E9K | x | x | x | x |
| | P6S/E9K | x | x | x | x |
| | S30N | x | x | x | x |
| | K53N/K56Q/E57D | x | x | x | x |
| | S30N/K53N/K56Q/E57D | x | x | x | x |
| | D238N | x | x | x | x |
| | Q509K | x | Δ | Δ | x |
| | Q509R | x | Δ | Δ | x |
| | Q509K/E744K | x | x | x | x |
| | Q509K/I709L/E710L | x | x | x | x |
| | I709L | x | x | x | x |
| | I709L/E710L | x | x | x | x |
| | I709L/E710K | x | x | x | x |
| | I709L/E710Q | x | x | x | x |
| | E710L | x | x | x | x |
| | E710K | x | x | x | x |
| | E710Q | x | x | x | x |
| | E744K | x | Δ | Δ | x |
| | E744R | x | Δ | Δ | x |
| | E799G | x | x | x | x |
| | E799G/E800A | x | x | x | x |
| Z05 | WT | x | x | x | x |
| | Q509K | x | Δ | Δ | x |
| | Q509R | x | Δ | Δ | x |
| | E744K | x | Δ | Δ | x |
| | E744R | x | Δ | Δ | x |

Example 4

High-Speed PCR

High-speed PCR in which the extension time was shortened was performed using the DNA polymerase produced in Example 2. For PCR, the buffer provided with KOD Dash (produced by Toyobo Co. Ltd.) was used, and 50 μl of a reaction solution containing 1×PCR buffer, 0.2 mM dNTPs, 15 pmol of primers for amplifying 3.6 kb of human β-globin (SEQ ID NOs: 6 and 7), 50 ng of human genomic DNA (produced by Roche), and 5 U of enzyme was subjected to preliminary reaction at 94° C. for 2 minutes. Thereafter, PCR was performed using a GeneAmp PCR System 9700 (Applied Biosystems) by repeating a cycle 35 times, each cycle consisting of 10 seconds at 98° C., 10 seconds at 60° C., and 15 seconds, 1 minute, or 2 minutes at 68° C. After completion of the reaction, 5 μl of each of the resulting reaction solutions was subjected to one percent agarose gel electrophoresis, followed by ethidium bromide staining to confirm the amount of amplified DNA fragments under ultraviolet irradiation.

Figure 2:
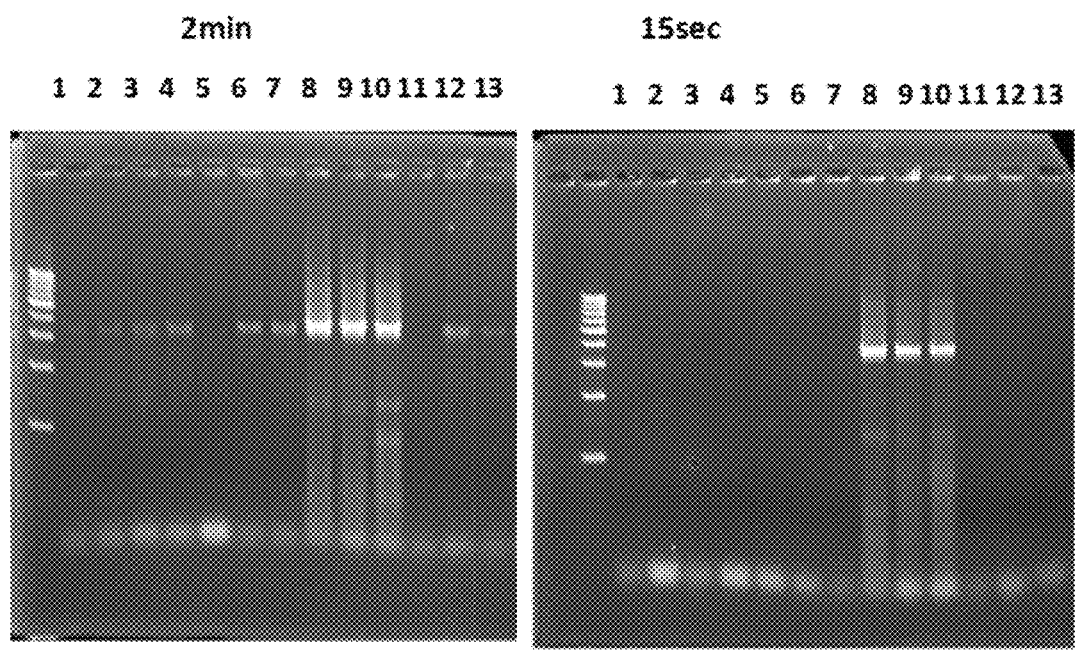
FIG. 2 shows the analytical results of DNA amplification by high-speed PCR in Example 4.

FIG. 2 shows the comparison results with respect to the amplification amounts of 3.6 kb of human β-globin, based on one percent agarose gel electrophoresis, between the extension time (reaction time at 68° C.) of 15 seconds and the extension time (reaction time at 68° C.) of 2 minutes in high-speed PCR using 5 U of Tth DNA polymerase and various modified Tth DNA polymerases (E9K, P6S/E9K, P6S, K53N/K56Q/E57D, S30N/K53N/K56Q/E57D, S30N, D238N, Q509K, Q509K, E744K, E799G, E799G/E800A). When the extension time was 2 minutes, the use of E9K, P6S/E9K, P6S, S30N/K53N/K56Q/E57D, S30N, D238N, Q509R, Q509K, E744K, and E799G/E800A allowed amplification; in particular, the use of Q509R, Q509K, and E744K produced clear intense bands. When the extension time was 15 seconds, only Q509R, Q509K, and E744K mutants allowed amplification.

Table 4 collectively shows the results of amplification performed as in Example 4 with the use of various DNA polymerases and mutants. ○ signifies that amplification was observed. Δ signifies that although amplification was observed, many bands were thin or nonspecific. X signifies that amplification was not observed.

The use of Taq DNA polymerase did not allow amplification for all of the amplification times, while the use of E507K, E507Q, E742K, and E742R mutants produced bands for all of the amplification times. Q509K, Q509R, E744K, and E744R mutants of Tth or Z05 DNA polymerase also produced bands for all of the amplification times, and produced clear bands for the amplification time of 15 seconds, in which the amplification amount was reduced with the use of E507K, E507Q, E742K, and E742R mutants of Taq DNA polymerase. The results revealed that the mutants of Tth or Z05 DNA polymerase that has reverse transcription activity showed more suitable performance for high-speed PCR, than general-purpose Taq DNA polymerase and the mutants thereof.

TABLE 4

| | | Amplification time | | |
|---|---|---|---|---|
| | | 15 seconds | 1 minute | 2 minutes |
| Taq | WT | x | x | x |
| | E507K | Δ | ○ | ○ |
| | E507R | Δ | ○ | ○ |
| | E742K | Δ | ○ | ○ |
| | E742R | Δ | ○ | ○ |
| Tth | WT | x | x | Δ |
| | P6S | x | x | Δ |
| | E9K | x | x | Δ |
| | P6S/E9K | x | x | Δ |
| | S30N | x | x | Δ |
| | K53N/K56Q/E57D | x | x | x |
| | S30N/K53N/K56Q/E57D | x | x | Δ |
| | D238N | x | x | Δ |
| | Q509K | ○ | ○ | ○ |
| | Q509R | ○ | ○ | ○ |
| | Q509K/E744K | x | x | Δ |
| | Q509K/I709L/E710L | x | x | Δ |
| | I709L | x | x | x |
| | I709L/E710L | x | x | x |
| | I709L/E710K | x | x | x |
| | I709L/E710Q | x | x | x |
| | E710L | x | x | Δ |
| | E710K | x | x | Δ |
| | E710Q | x | x | Δ |
| | E744K | ○ | ○ | ○ |
| | E744R | ○ | ○ | ○ |
| | E799G | x | x | x |
| | E799G/E800A | x | x | Δ |
| Z05 | WT | x | x | Δ |
| | Q509K | ○ | ○ | ○ |
| | Q509R | ○ | ○ | ○ |
| | E744K | ○ | ○ | ○ |
| | E744R | ○ | ○ | ○ |

Example 5

Direct Amplification from Blood

PCR was performed using the DNA polymerase produced in Example 2 by directly adding blood to the reaction solution. For PCR, the buffer provided with KOD Dash (produced by Toyobo Co. Ltd.) was used, and 50 μl of a reaction solution containing 1×PCR buffer, 0.2 mM dNTPs, 15 pmol of primers for amplifying 3.6 kb of human β-globin (SEQ ID NOs: 6 and 7), 1 µl, 3 µl, or 5 µl of blood, and 5 U of enzyme was subjected to preliminary reaction at 94° C. for 2 minutes. Thereafter, PCR was performed using a GeneAmp PCR System 9700 (Applied Biosystems) by repeating a cycle 35 times, each cycle consisting of 10 seconds at 98° C., 10 seconds at 60° C., and 4 minutes at 68° C. After completion of the reaction, 5 µl of each of the resulting reaction solutions was subjected to one percent agarose gel electrophoresis, followed by ethidium bromide staining to confirm the amount of amplified DNA fragments under ultraviolet irradiation.

Figure 3:
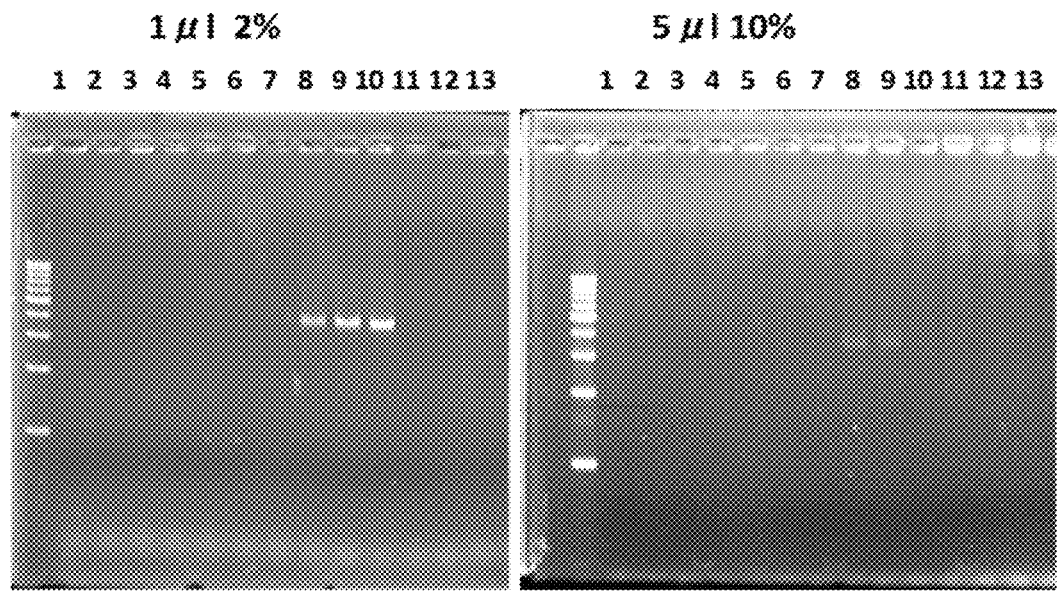
FIG. 3 shows the analytical results of DNA amplification in a blood sample in Example 5.

FIG. 3 shows the comparison results with respect to the amplification amounts of 3.6 kb of human β-globin, based on one percent agarose gel electrophoresis, between the amounts of blood (1 µl and 5 µl) added to the reaction solution with the use of 5 U of Tth DNA polymerase and various modified Tth DNA polymerases (E9K, P6S/E9K, P6S, K53N/K56Q/E57D, S30N/K53N/K56Q/E57D, S30N, D238N, Q509R, Q509K, E744K, E799G, and E799G/E800A). When 1 µl of blood was added for amplification, the use of Q509R, Q509K, and E744K produced clear bands. When 5 µl of blood was added, the use of Q509R and Q509K mutants allowed amplification, although the amplification amounts were reduced.

Table 5 collectively shows the results of amplification from 1 µl, 3 µl, and 5 µl of blood using various DNA polymerases and mutants. ○ signifies that amplification was observed. Δ signifies that although amplification was observed, many bands were thin or nonspecific. X signifies that amplification was not observed.

The results confirmed that although the use of Taq DNA polymerase did not allow amplification from blood, the use of E507K, E507Q, E742K, and E742R mutants allowed amplification from 1 µl of blood. When a higher amount of blood was added, the use of Taq DNA polymerase or the mutants thereof did not allow amplification. In terms of Tth and Z05 DNA polymerases, the wild-type polymerases and most of the mutants did not allow amplification; however, Q509K, Q509R, E744K, and E744R mutants allowed amplification from 1 and 3 µl of blood. Even from 5 µl of blood, the use of Q509K and Q509R mutants of Tth DNA polymerase allowed amplification. The results confirmed that the mutants of Tth and Z05 DNA polymerases that have reverse transcription activity were less inhibited by blood, compared to general-purpose Taq DNA polymerase and the mutants thereof.

TABLE 5

|     |     | Blood |     |     |
| --- | --- | --- | --- | --- |
|     |     | 1 µl | 3 µl | 5 µl |
| Taq | WT | x | x | x |
|     | E507K | Δ | x | x |
|     | E507R | Δ | x | x |
|     | E742K | Δ | x | x |
|     | E742R | Δ | x | x |
| Tth | WT | x | x | x |
|     | P6S | x | x | x |
|     | E9K | x | x | x |
|     | P6S/E9K | x | x | x |
|     | S30N | x | x | x |
|     | K53N/K56Q/E57D | x | x | x |
|     | S30N/K53N/K56Q/E57D | x | x | x |
|     | D238N | x | x | x |
|     | Q509K | o | o | Δ |
|     | Q509R | o | o | Δ |
|     | Q509K/E744K | x | x | x |

TABLE 5-continued

|     |     | Blood |     |     |
| --- | --- | --- | --- | --- |
|     |     | 1 µl | 3 µl | 5 µl |
|     | Q509K/I709L/E710L | x | x | x |
|     | I709L | x | x | x |
|     | I709L/E710L | x | x | x |
|     | I709L/E710K | x | x | x |
|     | I709L/E710Q | x | x | x |
|     | E710L | x | x | x |
|     | E710K | x | x | x |
|     | E710Q | x | x | x |
|     | E744K | o | o | x |
|     | E744R | o | o | x |
|     | E799G | x | x | x |
|     | E799G/E800A | x | x | x |
| Z05 | WT | x | x | x |
|     | Q509K | o | o | x |
|     | Q509R | o | o | x |
|     | E744K | o | o | x |
|     | E744R | o | o | x |

Example 6

RT-PCR Using DNA Polymerase with Reverse Transcription Ability

A single-step RT-PCR from RNA was performed using the DNA polymerase produced in Example 2. For RT-PCR, the buffer provided with TKOD-Plus-Ver. 2 (produced by Toyobo Co. Ltd.) was used, and 200 ng, 20 ng, 2 ng, or 0.2 ng of HeLa total RNA was added to 20 µl of a reaction solution containing 1×PCR buffer, 2.5 mM Mn(OAc)2, 0.4 mM dNTPs, 0.4 pmol of primers for amplifying human β-globin (SEQ ID NOs: 10 and 11), SYBR (registered trademark) Green I (diluted 1:30000), and 1 U of antibody-mixed enzyme. After preliminary reaction at 90° C. for 30 seconds, a reverse transcription reaction was performed at 61° C. for 20 minutes, followed by the preliminary reaction again at 95° C. for 60 seconds. Thereafter, real-time PCR was performed using LC96 (produced by Roche) by repeating a cycle 40 times, each cycle consisting of 15 seconds at 95° C., 15 seconds at 60° C., and 45 minutes at 74° C. As the enzyme, Tth DNA polymerase and the modified Tth DNA polymerases (Q509K, E744R) were used.

Figure 4:
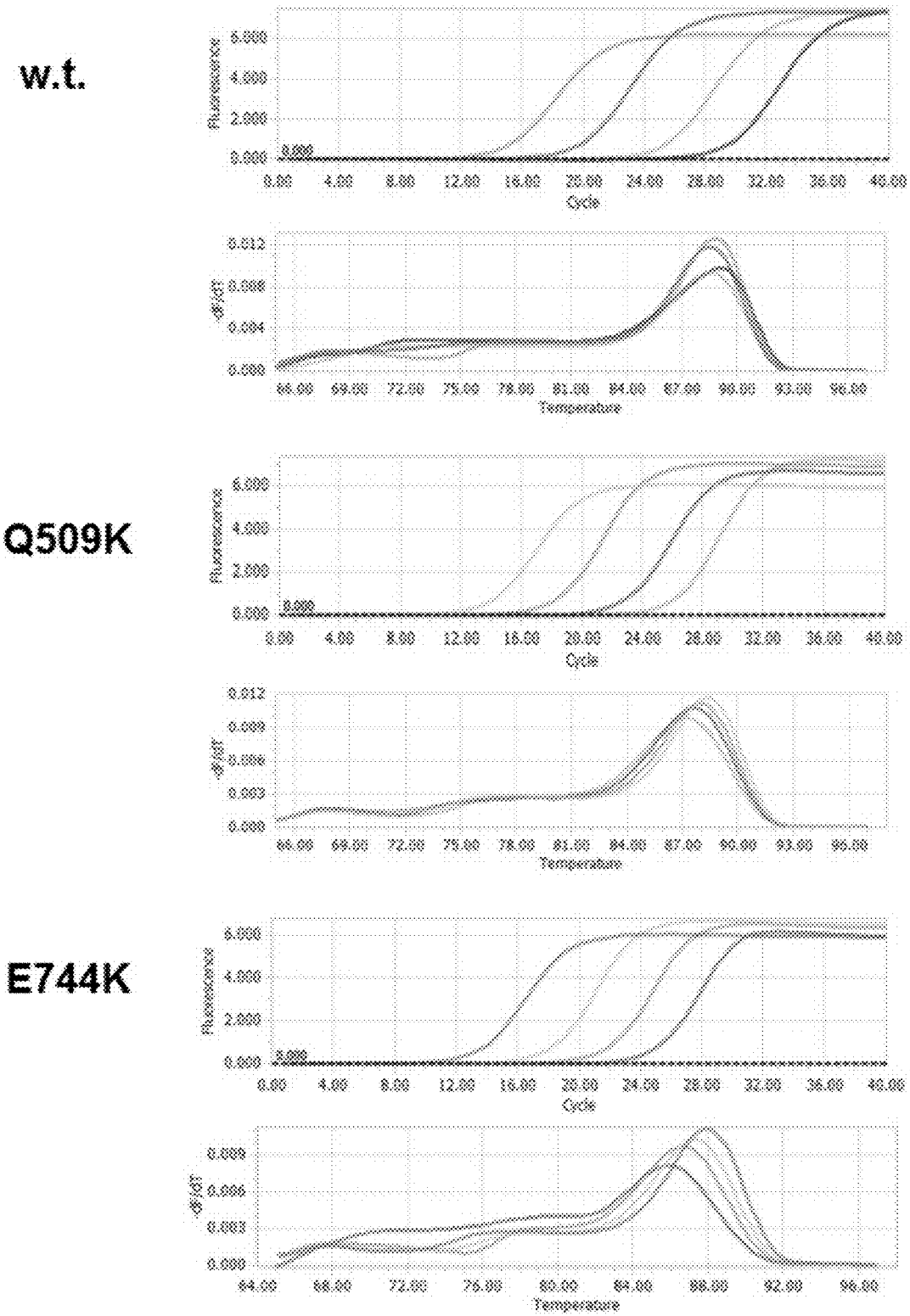
FIG. 4 are graphs showing the results of the RT-PCR amplification curves and melting curves obtained in Example 6.

FIG. 4 shows the results of the amplification curves and melting curves of RT-PCR. Table 6 collectively shows the results of the Cq values and PCR efficiency. The curves of the wild-type Tth DNA polymerase rose slowly, and the reaction efficiency was as low as less than 60%, while the curves of the mutants rose quickly, and the PCR efficiency was as high as 70 to 80%. The results confirmed that modification improved the performance. In RT-PCR as well, in which Taq DNA polymerase cannot be used, the modification of Tth DNA polymerase having reverse transcription ability was more advantageous.

TABLE 6

|     | WT | Q509K | E744K |
| --- | --- | --- | --- |
| 200 ng | 12.94 | 12.08 | 11.75 |
| 20 ng | 17.63 | 16.33 | 16.17 |
| 2 ng | 23.59 | 20.82 | 19.81 |
| 0.2 ng | 27.72 | 24.61 | 23 |
| H2O | — | — | — |
| Slope | −5.030 | −4.208 | −3.739 |
| PCR efficiency | 58.1% | 72.8% | 85.1% |
| R2 | 0.996 | 0.999 | 0.995 |

Example 7

RT-PCR Using DNA Polymerase with Reverse Transcription Ability

A single-step RT-PCR from RNA was performed using the DNA polymerase produced in Example 2. For RT-PCR, the buffer provided with KOD-Plus-Ver. 2 (produced by Toyobo Co. Ltd.) was used, and 10 ng, 1 ng, 0.1 ng, or 0.01 ng of HeLa total RNA was added to 20 µl of a reaction solution containing 1×PCR buffer, 2.5 mM Mn(OAc)2, 0.4 mM dNTPs, 4 pmol of primers for amplifying β-actin (SEQ ID NOs: 10 and 11), SYBR (registered trademark) Green I (diluted 1:30000), and 1 U of antibody-mixed enzyme. After preliminary reaction at 90° C. for 30 seconds, a reverse transcription reaction was performed at 60° C. for 1, 5 or 10 minutes, followed by the preliminary reaction again at 95° C. for 60 seconds. Thereafter, real-time PCR was performed using LC96 (produced by Roche) by repeating a cycle 45 times, each cycle consisting of 15 seconds at 95° C. and 60 seconds at 60° C. As the enzyme, Tth DNA polymerase and the modified Tth DNA polymerases (Q509R, E744K) were used.

Figure 5:
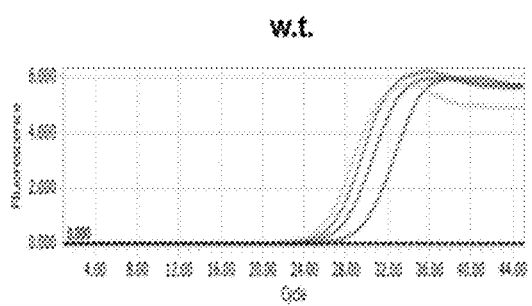
FIG. 5 are graphs showing the results of the RT-PCR amplification curves and melting curves obtained using wild-type Tth DNA polymerase and modified Tth DNA polymerases in Example 7.
Figure 5:
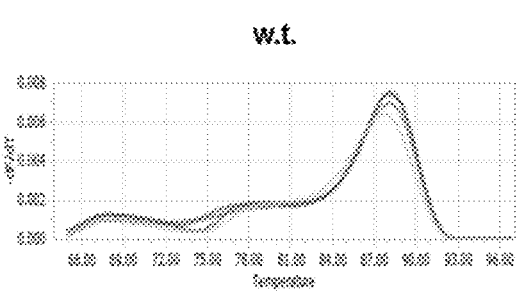
Figure 5:
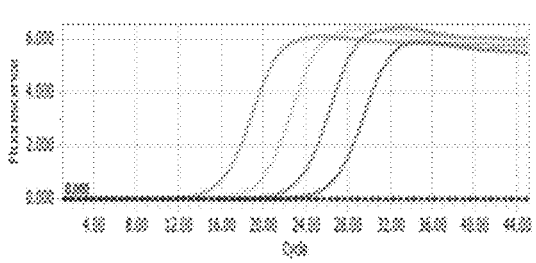
Figure 5:
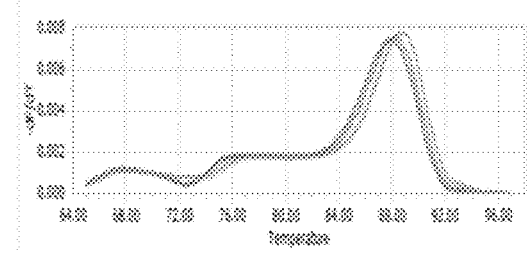
Figure 5:
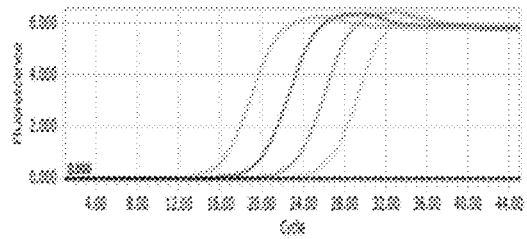
Figure 5:
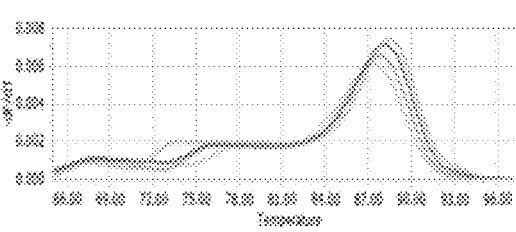
Figure 5:
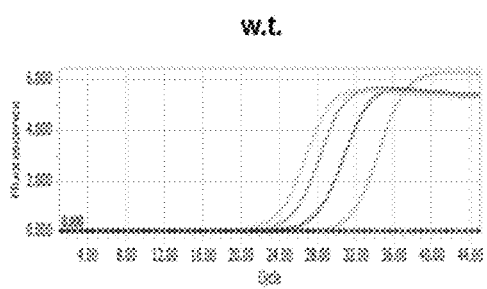
Figure 5:
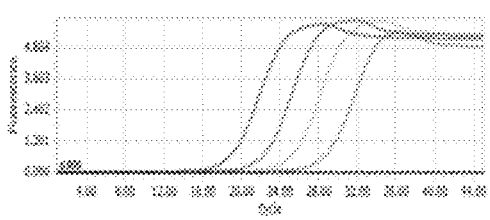
Figure 5:
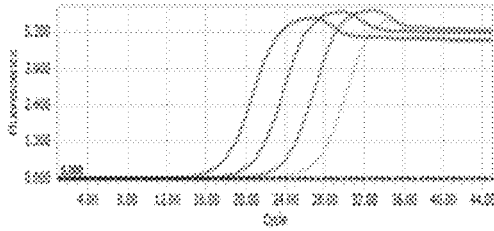
Figure 5:
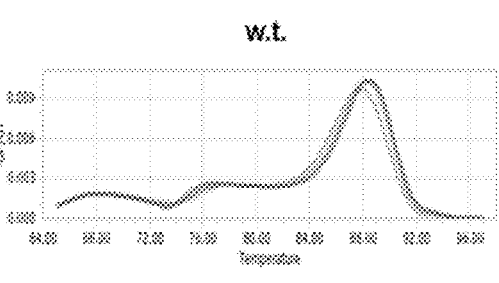
Figure 5:
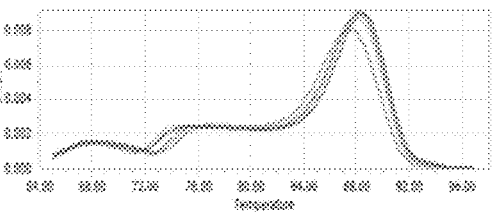
Figure 5:
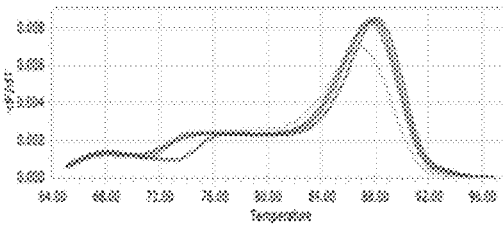
Figure 5:
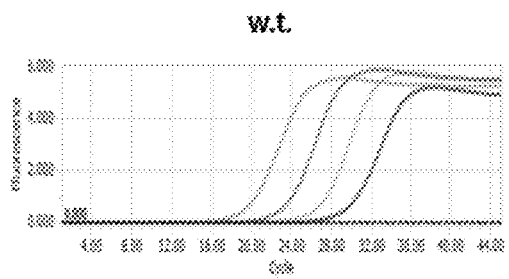
Figure 5:
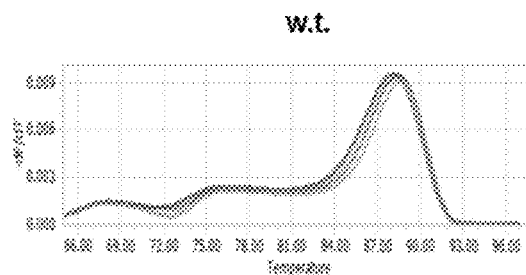
Figure 5:
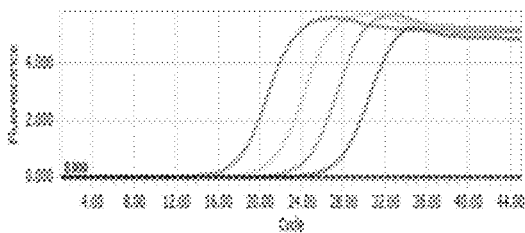
Figure 5:
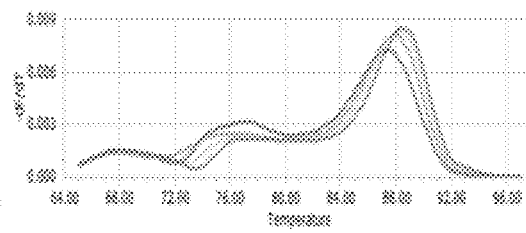
Figure 5:
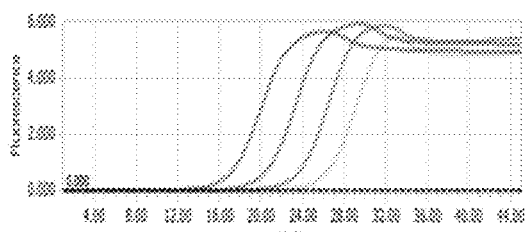
Figure 5:
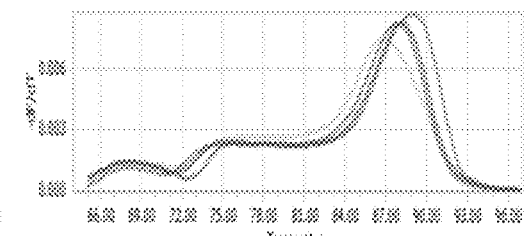

FIG. 5 collectively shows the results of the amplification curves, melting curves, Ct values, and PCR efficiency of RT-PCR. For the wild-type Tth DNA polymerase, a shorter reverse transcription time resulted in smaller Ct value intervals; when the reverse transcription time was 1 minute, $r^2$ was as considerably low as 0.947, and, additionally, the PCR efficiency was 586%, which was far outside the suitable range of 90 to 110%. In contrast, for the mutants, even when the reverse transcription time was short, i.e., when the reverse transcription time was 1 minute, $r^2$ was as high as 0.998 and 0.999; and, additionally, the PCR efficiency was 93% and 95%, which was within the suitable range of 90 to 110%. The results confirmed that the modification improved the performance. In RT-PCR as well, in which Taq DNA polymerase cannot be used, the modification of DNA polymerase having reverse transcription ability was more advantageous.

Example 8

Storage Stability of Modified Tth DNA Polymerase (Q509K, Q509R)

The storage stability of master mixes comprising the Tth DNA polymerase (Q509K or Q509R) produced in Example 2 was evaluated. For the master mixes, the buffer provided with KOD-Plus-Ver. 2 (produced by Toyobo Co. Ltd.) was used, and 2× master mixes each containing 0.4 mM dNTPs and 1 U of antibody-mixed enzyme in a 20 µl system were prepared. The resulting products were stored for 4 weeks at −20° C. or 37° C. to evaluate the difference between the stabilities of the modified Tth DNA polymerases (Q509K and Q509R). As an evaluation system, a single-step RT-PCR from RNA was performed. Here, the prepared master mixes were used, and enterovirus RNA in an amount equivalent to 625 copies was added to 20 µl of a reaction solution containing 1× master mix, 2.5 mM Mn(OAc)2, 10 pmol of primers (SEQ ID NOs: 12 and 13), 4 pmol of probe (SEQ ID NO: 14), and 1 U of antibody-mixed enzyme, and the resulting mixture was subjected to preliminary reaction at 90° C. for 30 seconds. Thereafter, a reverse transcription reaction was performed at 60° C. for 5 minutes, followed by the preliminary reaction again at 95° C. for 60 seconds. Thereafter, real-time PCR was performed using LC96 (produced by Roche) by repeating a cycle 45 times, each cycle consisting of 5 seconds at 95° C. and 5 seconds at 60° C.

The results shown in Table 7 revealed that when stored at 37° C. for 4 weeks, only the modified Tth DNA polymerase (Q509R) allowed amplification; that is, Q509R mutant showed higher stability. The reason for this is considered to be as follows. The amino group on the side chain of lysine has higher nucleophilicity than the guanidine group on the side chain of arginine; and has higher reactivity, which caused a chemical reaction to occur with the buffer components, resulting in low stability.

TABLE 7

|  | −20° C. 4 weeks | 37° C. 4 weeks |
| --- | --- | --- |
| Q509K | 32.4 | — |
| Q509R | 31.9 | 34.83 |

Example 9

Direct Amplification from Blood Stored on FTA Card

PCR was carried out using the DNA polymerase produced in Example 2 by directly adding blood to a reaction solution. For PCR, the buffer provided with KOD FX (produced by Toyobo Co. Ltd.) was used, and 50 µl of a reaction solution containing 1×PCR buffer, 0.4 mM dNTPs, 15 pmol of primers for amplifying 1.3 kb of human β-globin (SEQ ID NOs: 15 and 16), one 1.2-mm φ punch removed from an FTA card (GE Healthcare) with blood, and 2 U of enzyme was subjected to preliminary reaction at 94° C. for 2 minutes. Thereafter, PCR was performed using a GeneAmp PCR System 9700 (Applied Biosystems) by repeating a cycle 30 times, each cycle consisting of 30 seconds at 94° C., 10 seconds at 60° C., and 2 minutes at 68° C. As enzymes, Tth DNA polymerase, the modified Tth DNA polymerases (Q509K, Q509R), Taq DNA polymerase, and the modified Taq DNA polymerases (E507K, E507R) were used after being mixed with an antibody. After completion of the reaction, 5 µl of each of the resulting reaction solutions was subjected to one percent agarose gel electrophoresis, followed by ethidium bromide staining to confirm the amount of amplified DNA fragments under ultraviolet irradiation.

Figure 6:
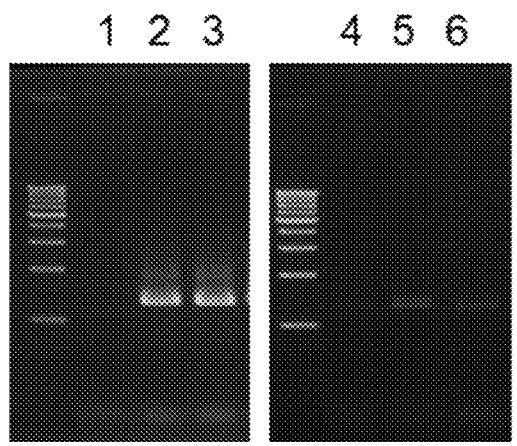
FIG. 6 shows the analytical results of DNA amplification from blood stored on an FTA card in Example 8.

FIG. 6 shows the comparison results with respect to the amplification amounts of 1.3 kb of human β-globin, based on one percent agarose gel electrophoresis, when blood stored on an FTA card (φ 1.2 mm) was added to the reaction solution while using 2 U of Tth DNA polymerase, the modified Tth DNA polymerases (Q509K, Q509R), Taq DNA polymerase, and the modified Taq DNA polymerases (E507K, E507R). Although the use of the wild-type Tth DNA polymerase, the wild-type Taq DNA polymerase, and the modified Taq DNA polymerases (E507K, E507R) did not allow amplification, the use of the modified Tth DNA polymerases (Q509K, Q509R) produced clear bands. To stabilize nucleic acid, an FTA card contains modifiers, such as guanidine, which are known to inhibit PCR. The results revealed that the mutants of the Tth DNA polymerase that has reverse transcription activity were less inhibited by FTA cards or blood than Taq DNA polymerase or the mutants thereof.

Example 10

Resistance of Modified Tth DNA Polymerase to Plasma-Derived Component

The influence when 40% of plasma was carried into the reaction solution was evaluated using the Tth DNA polymerase produced in Example 2. Specifically, *Escherichia coli* genomic DNA was spiked, and real-time PCR was carried out. For PCR, the buffer provided with a THUNDERBIRD(registered trademark) Probe One-step qRT-PCR Kit (produced by Toyobo Co. Ltd.) was used, and 5 ng, 0.5 ng, 0.05 ng, or 0.005 ng of *Escherichia coli* genomic DNA was added to 20 μl of a reaction solution containing 1×PCR buffer, 4 pmol of *Escherichia coli*-specific primers (SEQ ID NOs: 17 and 18), 4 pmol of probe (SEQ ID NO: 19), 1 U of antibody-mixed enzyme, and 8 μl of plasma. After preliminary reaction at 95° C. for 1 minute, real-time PCR was performed by repeating a cycle 40 times, each cycle consisting of 15 seconds at 95° C. and 15 seconds at 60° C. For the enzyme, Tth DNA polymerase and the modified Tth DNA polymerase (Q509R) were used.

Figure 7:
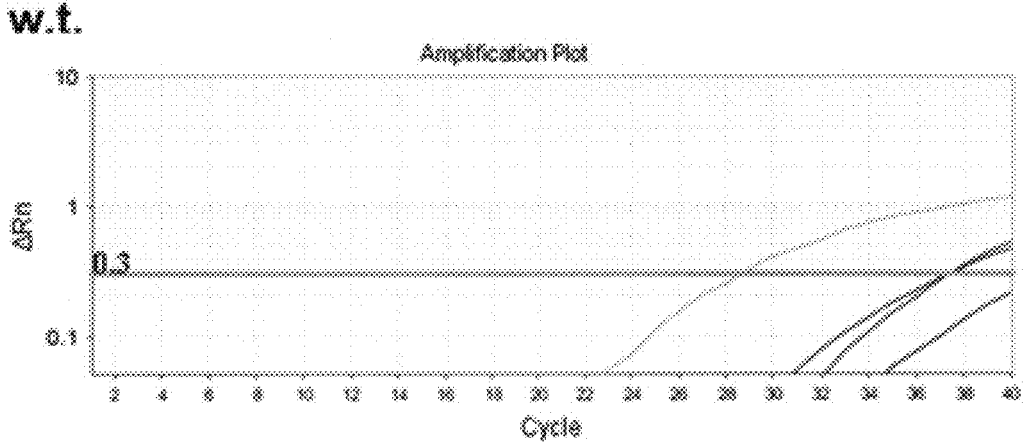
FIG. 7 are graphs showing the evaluation results on the resistance of DNA polymerases to plasma-derived components in Example 10.
Figure 7:
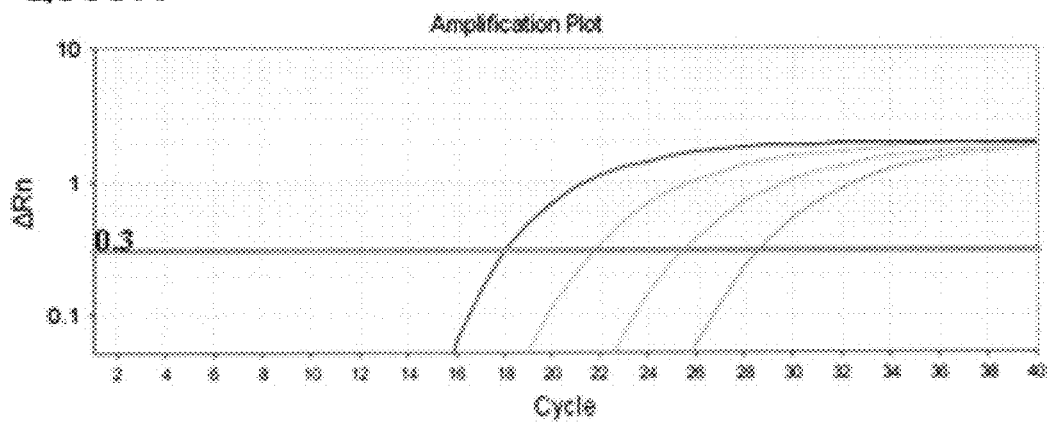

FIG. 7 collectively shows the results of the amplification curves, Ct values, and PCR efficiency of RT-PCR. The wild-type Tth DNA polymerase was inhibited by plasma, and $r^2$ was as considerably low as 0.5801. Further, the PCR efficiency was 149%, which was far outside the suitable range of 90 to 110%. In contrast, for Q509R mutant, even when the reverse transcription time was short, i.e., when the reverse transcription time was 1 minute, $r^2$ was as high as 0.998; and, additionally, the PCR efficiency was 92%, which was within the suitable range of 90 to 110%. The results confirmed that the modification improved the resistance to plasma-derived components.

Example 11

High-Speed RT-PCR Detection

A single-step RT-PCR from enterovirus RNA was performed using the Tth DNA polymerase (Q509R) produced in Example 2. For RT-PCR, the buffer provided with KOD-Plus-Ver. 2 (produced by Toyobo Co. Ltd.) was used, and enterovirus RNA in an amount equivalent to 2500, 625, 156, 40, or 24.4 copies was added to 20 μl of a reaction solution containing 1×PCR buffer, 2.5 mM Mn(OAc)2, 0.4 mM dNTPs, 10 pmol of primers (SEQ ID NOs: 12 and 13), 4 pmol of probe (SEQ ID NO: 14), and 1 U of antibody-mixed enzyme. After preliminary reaction at 90° C. for 30 seconds, a reverse transcription reaction was performed at 60° C. for 5 minutes, followed by the preliminary reaction again at 95° C. for 60 seconds. Thereafter, real-time PCR was performed using LC96 (produced by Roche) by repeating a cycle 50 times, each cycle consisting of 5 seconds at 95° C., and 5 seconds at 60° C. For the enzyme, Tth DNA polymerase and the modified Tth DNA polymerase (Q509R) were used.

Figure 8:
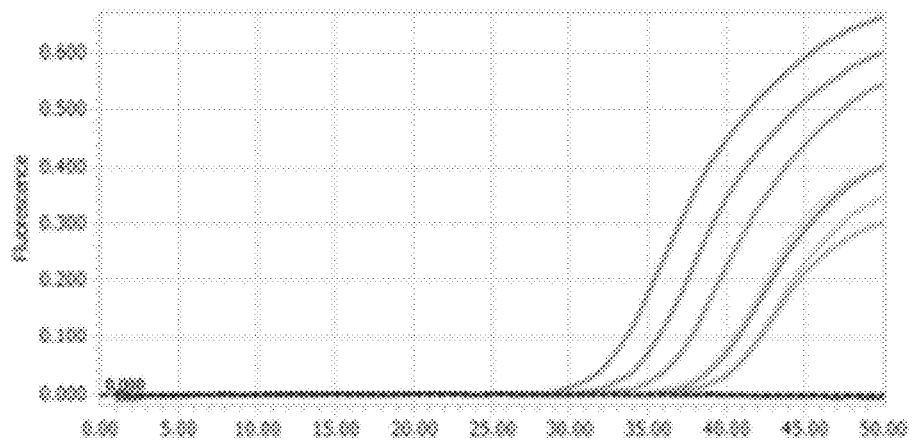
FIG. 8 are graphs showing the evaluation results on high-speed RT-PCR using DNA polymerases in Example 11.
Figure 8:
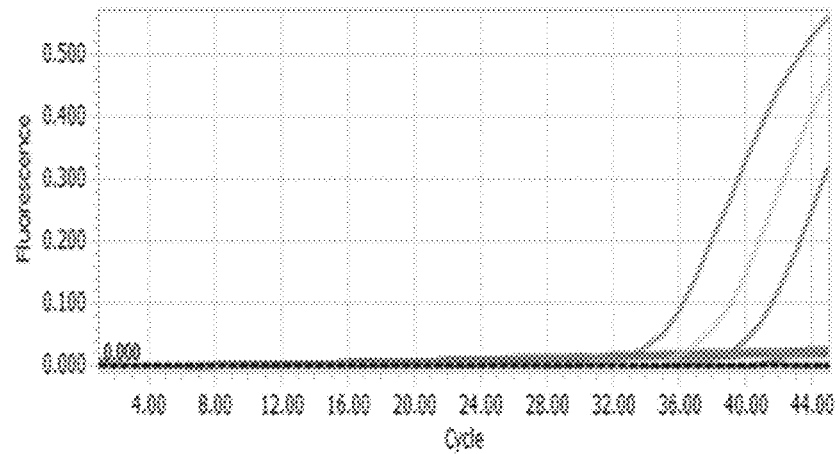

The results shown in FIG. 8 revealed that, in high-speed RT-PCR, the use of the modified Tth DNA polymerase (Q509R) allowed more stable detection of 24.4 copies of enteroviruses than the use of the wild-type Tth DNA polymerase.

Example 12

Resistance of Modified Tth DNA Polymerase to Blood

Real-time PCR was carried out using the Tth DNA polymerase produced in Example 2. For PCR, the buffer provided with a THUNDERBIRD(registered trademark) Probe One-step qRT-PCR Kit (produced by Toyobo Co. Ltd.) was used, and 20 μl of a reaction solution containing 1×PCR buffer, 4 pmol of primers (SEQ ID NOs: 20 and 21), 4 pmol of probe (SEQ ID NO: 22), 4 U of antibody-mixed enzyme, and 1 μl of plasma was prepared and subjected to preliminary reaction at 95° C. for 1 minute. Thereafter, real-time PCR was performed by repeating a cycle 40 times, each cycle consisting of 15 seconds at 95° C. and 60 seconds at 60° C. For the enzyme, Tth DNA polymerase and the modified Tth DNA polymerases (Q509R, E744R) were used.

Figure 9:
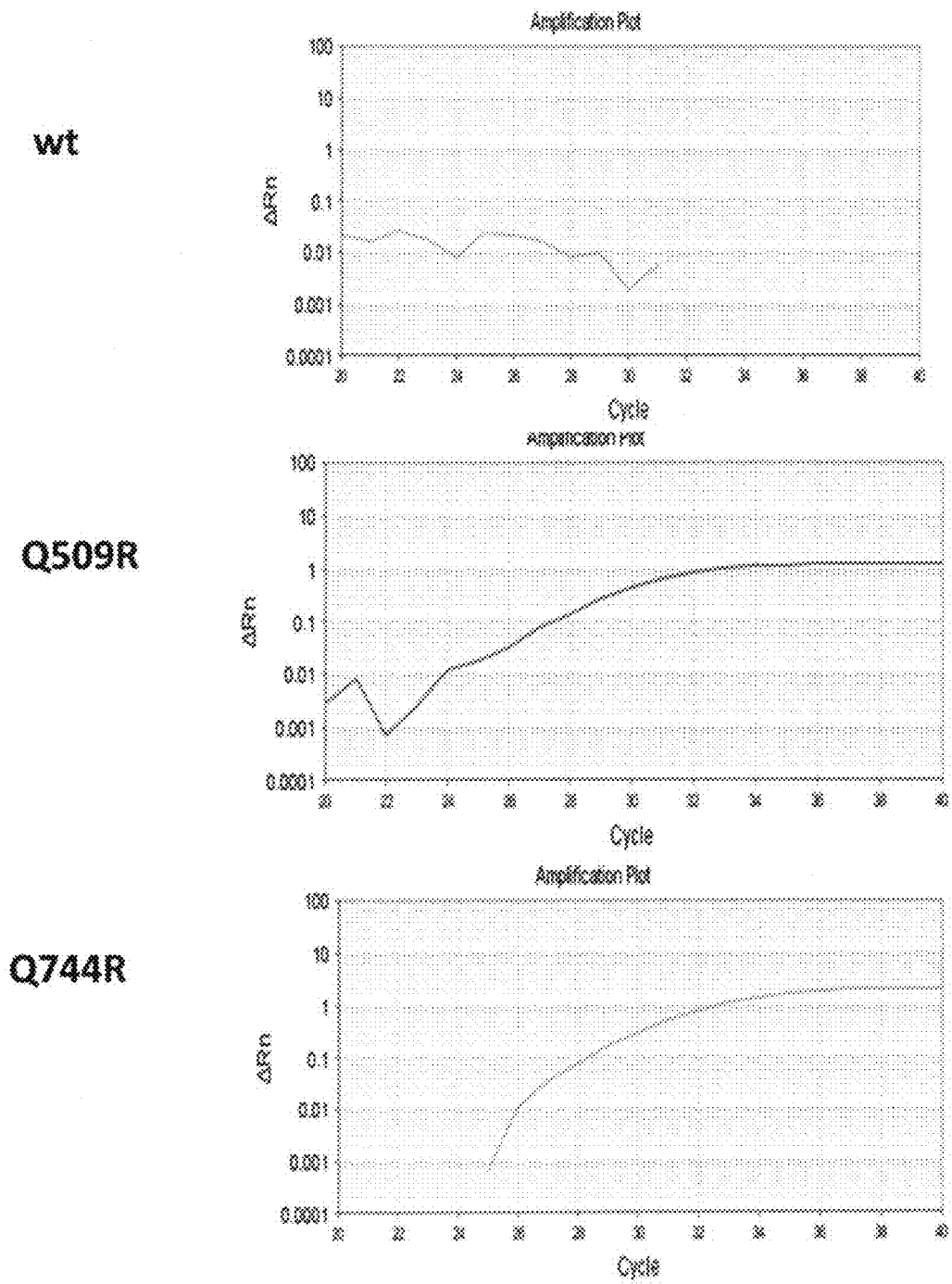
FIG. 9 are graphs showing the evaluation results on the resistance of DNA polymerases to blood in Example 12.

As shown in FIG. 9, although the use of the wild-type Tth DNA polymerase did not allow amplification, the use of the modified Tth DNA polymerases (Q509R, E744K) allowed amplification from blood.

INDUSTRIAL APPLICABILITY

The present invention provides modified DNA polymerases that are useful in the field of molecular biology, and compositions thereof. The present invention enables further shortening of reaction time without reaction inhibition during nucleic acid amplification. The present invention is particularly useful for gene expression analysis, and is applicable not only to research purposes, but also to clinical diagnosis, environmental testing, etc.

---

The invention claimed is:

1. A reverse transcription method comprising reverse transcribing a nucleic acid sequence in a biological sample that is not purified using a DNA polymerase having reverse transcription activity and having 93% or more identity to the amino acid sequence of SEQ ID NO: 1 or SEQ ID NO: 2,
wherein the biological sample is at least one selected from the group consisting of tissues of animals, body fluids, excrement, cells, bacteria, and viruses, and
wherein the reverse transcription is completed in 5 minutes or less, and the DNA polymerase comprises an amino acid substitution with arginine at position 509.

2. The reverse transcription method according to claim 1, wherein the DNA polymerase has 96% or more identity to the amino acid sequence of SEQ ID NO: 1 or SEQ ID NO: 2.

3. The reverse transcription method according to claim 1, wherein the DNA polymerase has an amino acid sequence that is 100% identical to the amino acid sequence of SEQ ID NO: 1 or SEQ ID NO: 2 except that the amino acid at position 509 is substituted with arginine.

4. The reverse transcription method according to claim 1, wherein the reverse transcription is completed in 1 minute or less.

5. A nucleic acid amplification method comprising amplifying a nucleic acid sequence in a biological sample that is not purified using a DNA polymerase having reverse transcription activity and having 93% or more identity to the amino acid sequence of SEQ ID NO: 1 or SEQ ID NO: 2,
wherein extension time per kb of nucleic acid sequence is 30 seconds or less,
wherein the biological sample is at least one selected from the group consisting of tissues of animals, body fluids, excrement, cells, bacteria, and viruses, and
wherein the DNA polymerase comprises an amino acid substitution with arginine at position 509.

6. The nucleic acid amplification method according to claim 5, wherein the DNA polymerase has 96% or more identity to the amino acid sequence of SEQ ID NO: 1 or SEQ ID NO: 2.

7. The nucleic acid amplification method according to claim 5, wherein the DNA polymerase has an amino acid sequence that is 100% identical to the amino acid sequence of SEQ ID NO: 1 or SEQ ID NO: 2 except that the amino acid at position 509 is substituted with arginine.

* * * * *